US010575974B2

(12) United States Patent
De Pablo Peña et al.

(10) Patent No.: US 10,575,974 B2
(45) Date of Patent: Mar. 3, 2020

(54) KIT FOR PLACING A BYPASS

(71) Applicant: Carag AG, Baar (CH)

(72) Inventors: Albora De Pablo Peña, Zurich (CH); Claudio Steiner, Baar (CH)

(73) Assignee: Carag AG, Baar (CH)

( * ) Notice: Subject to any disclaimer, the term of this patent is extended or adjusted under 35 U.S.C. 154(b) by 0 days.

(21) Appl. No.: 15/302,978

(22) PCT Filed: Apr. 2, 2015

(86) PCT No.: PCT/EP2015/057389
§ 371 (c)(1),
(2) Date: Oct. 7, 2016

(87) PCT Pub. No.: WO2015/155134
PCT Pub. Date: Oct. 15, 2015

(65) Prior Publication Data
US 2017/0035591 A1     Feb. 9, 2017

(30) Foreign Application Priority Data

Apr. 10, 2014 (EP) .................................... 14164307

(51) Int. Cl.
*A61F 2/958* (2013.01)
*A61F 2/06* (2013.01)
(Continued)

(52) U.S. Cl.
CPC ........ *A61F 2/958* (2013.01); *A61B 17/00234* (2013.01); *A61B 17/11* (2013.01);
(Continued)

(58) Field of Classification Search
CPC ............ A61B 17/11; A61B 2017/1107; A61B 2017/1139; A61B 2017/00252;
(Continued)

(56) References Cited

U.S. PATENT DOCUMENTS

| 5,904,697 A * | 5/1999 | Gifford, III .......... A61B 17/064 606/153 |
| 2002/0091435 A1 | 7/2002 | Campbell |

(Continued)

FOREIGN PATENT DOCUMENTS

| WO | 98/19636 A2 | 5/1998 |
| WO | 98/38939 A1 | 9/1998 |

(Continued)

*Primary Examiner* — Diane D Yabut
(74) *Attorney, Agent, or Firm* — McDonnell Boehnen Hulbert & Berghoff LLP

(57) ABSTRACT

A kit for placing a bypass between two body vessels (R, L) of a patient comprises two catheters (10, 11), two guide wires (30, 31) moveable within one of the catheters (10, 11) each and a bypass element delivery system (52, 53, 8) for holding a bypass element (6, 7). The bypass element delivery system (52, 53, 8) is moveable along the first guide wire (30) and the bypass element delivery system (52, 53, 8) is capable of releasing and setting free the bypass element (6, 7). The kit further comprises an expansible element (40) being capable of connecting with the bypass element delivery system (52, 53, 8), of moving the bypass element delivery system (52, 53, 8) towards the opposite end of the first guide wire (30) and of setting the bypass element delivery system (52, 53, 8) free. The inventive kit enables an atraumatic placement of a bypass.

15 Claims, 39 Drawing Sheets

(51) Int. Cl.
*A61B 17/11* (2006.01)
*A61B 17/00* (2006.01)
A61B 17/34 (2006.01)
A61B 17/06 (2006.01)

(52) U.S. Cl.
CPC ............... *A61F 2/06* (2013.01); *A61F 2/064* (2013.01); *A61B 17/3478* (2013.01); *A61B 2017/00252* (2013.01); *A61B 2017/00349* (2013.01); *A61B 2017/06104* (2013.01); *A61B 2017/1107* (2013.01); *A61B 2017/1135* (2013.01); *A61B 2017/1139* (2013.01); *A61F 2220/0016* (2013.01)

(58) Field of Classification Search
CPC ... A61B 2017/00349; A61B 2017/1135; A61F 2/064
See application file for complete search history.

(56) References Cited

U.S. PATENT DOCUMENTS

2003/0195457 A1   10/2003   LaFontaine et al.
2010/0069820 A1   3/2010    Zotz

FOREIGN PATENT DOCUMENTS

WO   98/38941 A1    9/1998
WO   12/092408 A1   7/2012

* cited by examiner

KIT FOR PLACING A BYPASS

This application is a US national phase of International Application No. PCT/EP2015/057389 filed on Apr. 2, 2015, which claims priority to European Patent Application No. 14164307.2 filed on Apr. 10, 2014, which are hereby incorporated by reference in their entirety.

TECHNICAL FIELD

The present invention relates to a kit for placing a bypass between a first and a second body vessel of a patient, a bypass element of this kit and a method for placing a bypass between a first and a second body vessel.

PRIOR ART

Coronary arteries can become partially restricted or completely clogged. This can lead to a heart attack. A number of systems and methods are known for treating such restricted or clogged arteries, such as expanding balloons or placing stents as well as medication. Percutaneous coronary artery bypass intervention is known as well. The advantage of this method is that the heart of the patient has not to be stopped during intervention. No open heart surgery and no lung machine are necessary with this method.

WO 98/38939 suggests to bypass a restriction in an artery (parent vessel) by accessing intraluminally a first site in the IMA (branch vessel) branching from the aorta. First, an occlusion is formed and an aperture is formed in the branching vessel. Then an aperture is formed in the parent vessel distal of the restriction and a conduit is provided to form a lumen which communicates between the branching vessel proximal of the occlusion and the parent vessel distal of the restriction. A graft is thereby connected between the branching vessel and the parent vessel. The kit used comprises a guide catheter enabling wires being introduced through the aorta into the branching vessel. A first wire introduces an occluding means for creating the occlusion in the branching vessel. After removal of the first wire, a second wire is introduced having a cutting device proximal to the newly occluded site of the branching vessel. The cutting device includes a proximal and a distal occluding balloon and a signal transmitter. A wire directed trough the artery comprises receivers receiving the signals of the transmitter. The IMA and the artery are cut and the graft forwarded trough the branching vessel to the artery in order to bypass the occluded site of the artery. This kit is quite complicated and expensive.

US 2003/0195457 discloses a percutaneous system for bypassing a restriction in a coronary artery wherein the system includes providing a graft having a body portion with a first end, a second end and a lumen there between. An aperture is formed in the aorta, the graft is inserted into the aorta and the first end of the graft is connected to the aorta about the aperture in the aorta. An aperture is then formed in the native vessel distal of the restriction. The second end of the graft is connected to the native vessel about the aperture therein such that the lumen in the graft communicates with the aorta and the native vessel. A signal transmitter and receivers are used to find the correct place for making the apertures. This publication further discloses a system including a wire and a snare. The distal tip of the wire includes a cutting edge. The snare as well comprises a cutting edge. The snare is used to capture the distal tip of the wire. The wire is then pulled back through the aperture in the aorta with the snare such that the wire extends all the way from within the distal portion of the native vessel up through the aperture of the aorta.

US 2010/0069820 shows a method and a kit for the performance of a bypass which does not need any of general anesthesia, extracorporeal circulation and chest opening. The kit comprises a partially flexible puncture needle and a covered stent. This puncture needle is used for making apertures in a first and a second body artery and the covered stent is used for connecting the two body arteries in order to establish a coronary artery bypass.

WO 98/19636 discloses a medical grafting method and apparatus using two wires and a push tube with a balloon for placing the graft of a coronary bypass.

SUMMARY OF THE INVENTION

It is an object of the invention to provide a new kit and a new method for placing a bypass between a first and a second body vessel of a patient.

The inventive kit for placing a bypass between a first and a second body vessel of a patient comprises
- a first catheter with a first delivery end and a second catheter with a second delivery end,
- a first guide wire moveable within the first catheter, the first guide wire having a first end region being moveable to the first delivery end, the first guide wire having an opposite end being opposite to the first end,
- a second guide wire moveable within the second catheter, the second guide wire having a second end being moveable to the second delivery end, the second end of the second guide wire being a catch for capturing the first end region of the first guide wire and for moving the first guide wire into the second catheter with the first end first,
- a bypass element delivery system for holding a bypass element, the bypass element delivery system being moveable along the first guide wire starting from the first end region of the first guide wire, wherein the bypass element delivery system is capable of releasing and setting free the bypass element and
- an expansible element, the expansible element being capable of connecting the bypass element delivery system and of moving the bypass element delivery system towards the opposite end of the first guide wire, the expansible element is capable of releasing the bypass element delivery system for setting the bypass element delivery system free.

This kit allows a bypass to be established in a minimum of time and risk for the patient. The treatment can be performed ambulatory and costs can be saved. Another advantage is that more patients can be treated, even a weak patient.

The kit is therefore applicable in a vascular bypass intervention, such as a coronary artery bypass intervention. The kit is applicable in percutaneous bypass interventions.

The expression "catheter" used in this text does also comprise elements such as "sheath".

In a preferred embodiment the expansible element is movable along the first guide wire from the opposite end towards the first end. In one embodiment the expansible element is an additional item. In another embodiment, the expansible element is the first catheter. Preferably, the expansible element captures the delivery system.

In a preferred embodiment, the expansible element is a balloon. This balloon is inflatable in a connecting end of the bypass element delivery system for capturing this system.

The balloon is deflatable for releasing the connecting end of the bypass element delivery system and for setting the bypass element delivery system free. Using a balloon reduces the risk of damaging any tissue material of the patient. Since the balloon can pull the delivery system through an aperture or a puncture of the clogged vessel, a higher force can be applied for moving the bypass element. In addition the balloon enables a smooth transition to the delivery system and this is less traumatic when entering the aperture of the clogged vessel, here the RIVA (ramus interventricularis anterior). In addition, the clogged vessel is only closed for a minimum of time.

The expansible element can preferably be slipped over the first guide wire and is preferably moveable relative to the first guide wire. In a preferred embodiment, the balloon encompasses the first guide wire.

In a preferred embodiment, the catch is a loop, a hook or forceps. The expression "loop" stands at least also for snare and lasso. When the catch is formed like a loop, snare or lasso and preferably being more flexible than the rest of the guide wire, the risk of damaging any tissue material of the patient is minimized.

Preferably the bypass element delivery system is moveable along the first guide wire in absence of the second guide wire and preferably also in absence of the second catheter. This reduces the space needed and is less traumatic.

The bypass element used for connecting the second with the first body vessel comprises preferably a graft and a stabilisation structure such as stent. The stabilisation structure is preferably expandable, for example self-expandable or balloon-expandable.

Preferably the stabilisation structure encompasses the graft. However, in other embodiments, the graft encompasses the stabilisation structure.

Since the first guide wire extends at some stage in both body vessels, the first guide wire has preferably a total length of at least 4 m.

In a preferred embodiment, the kit further comprises a first needle moveable within the first catheter to the first delivery end and a second needle moveable within the second catheter to the second delivery end. This enables to puncture both body vessels from their inside. The puncture is more precise than a puncture from the outside and the needle can move synchronously with the heartbeat. The risk of carrying body material from the outside of the vessels into them is minimized as well as piercing through the vessel. In addition the tools used can be minimized and adapted to the vessel.

Preferably, at least the first needle, preferably both needles are hollow. A hollow first needle enables the first guide wire to be moved within and relative to this first needle, so that the first needle can act as a duct to move the first guide wire out of the body vessel.

The bypass element to be hold in the bypass element delivery system of the inventive kit comprises a graft and a stabilization structure, such as a stent. The stabilisation structure is preferably expandable, for example self-expandable or balloon-expandable. In the following the expression "stent" is used, however other stabilization structures are meant as well. Graft and stent are arranged concentrically to each other, wherein the stent preferably encompasses the graft. When the stent comprises at least one end with anchoring elements, it can be fixed within the body vessel. The stent can comprise such anchoring elements at one end only or at both ends.

In another preferred embodiment, the graft comprises an end forming a widening, said widening being reinforced and acting as an anchoring element. The graft can be used without a stent or with a stent. In case a stent is used, the stent may have anchoring elements at its other end, i.e. the ends opposite the widened end of the graft. The graft itself can have such widened ends on both sides.

In another embodiment of the invention the kit for placing a bypass between a first and a second body vessel of a patient comprises:
  a first catheter with a first delivery end and a second catheter with a second delivery end,
  a first guide wire moveable within the first catheter, the first guide wire having a first end region being moveable to the first delivery end, the first guide wire having an opposite end being opposite to the first end region,
  a second guide wire moveable within the second catheter, the second guide wire having a second end being moveable to the second delivery end, the second end of the second guide wire being a catch for capturing the first guide wire and for moving the first guide wire into the second catheter with a first end region of the first guide wire first, and
  a first puncturing element moveable within the first catheter to the first delivery end and a second puncturing element moveable within the second catheter to the second delivery end, the first puncturing element being capable of puncturing the first vessel from the inside and the second puncturing element being capable of puncturing the second vessel from the inside.

Preferably the first puncturing element is a first needle and the second puncturing element is a second needle.

In this embodiment no expansible element may be present. The needles can be hollow or solid and they can be straight or bent, wherein the needle can be different from each other.

The inventive method for placing a bypass between a first body vessel and a second body vessel of a patient comprises the following steps:
  providing a first catheter with a first delivery end and a second catheter with a second delivery end,
  providing a first needle and a second needle,
  providing a first guide wire having a first end region and an opposite end being opposite to the first end,
  moving said first catheter within the first body vessel and moving said first needle within said first catheter and puncturing said first vessel from an inside of the first vessel,
  moving said second catheter within the second body vessel and moving said second needle within said second catheter and puncturing said second vessel from an inside of the second vessel,
  moving said first guide wire within the first catheter, thereby moving the first end region to the first delivery end,
  providing a second guide wire having a second end, the second end being a catch,
  moving said second guide wire within the second catheter, thereby moving the catch to the second delivery end,
  capturing the first end region with the catch and moving the captured first guide wire into the second catheter with the first end region first,
  providing a bypass element delivery system and a bypass element, the bypass element delivery system holding the bypass element,
  moving the bypass element delivery system along the first guide wire starting from the first end region of the first guide wire,
  providing an expansible element,
  moving the expansible element along the first guide wire from the opposite end towards the first end region, connecting the bypass element delivery system with the expansible and moving the bypass element delivery system towards the opposite end of the first guide wire, releasing the bypass element delivery system from the expansible element and releasing the bypass element from the bypass element delivery system and setting free the bypass element.

Further embodiments and variants of the invention are laid down in the dependent claims.

BRIEF DESCRIPTION OF THE DRAWINGS

A preferred embodiment of the invention is described in the following with reference to the drawings, which are for the purpose of illustrating the present preferred embodiment of the invention and not for the purpose of limiting the same. The drawings show in FIG. 1 schematically a LIMA (left internal mammary artery) and a RIVA (ramus interventricularis anterior), the RIVA comprising a constriction;

FIG. 24b a perspective view of the end according to FIG. 24a;

FIG. 25b a perspective view of the end according to FIG. 25a;

FIG. 26b a perspective view of the end according to FIG. 26a;

FIG. 27b an enlarged section of FIG. 27a;

FIG. 27c a longitudinal section of the end according to FIG. 27a;

FIG. 27d a front view of the end according to FIG. 27a;

FIG. 28b a top view of the end according to FIG. 28a;

FIG. 28c a side view of the end according to FIG. 28a;

FIG. 28d a front view of the end according to FIG. 28a;

Same elements are marked with the same reference numbers.

DESCRIPTION OF PREFERRED EMBODIMENTS

FIGS. 1 to 23 show a preferred embodiment of the inventive intervention kit in a preferred implementation.

Figure 1:
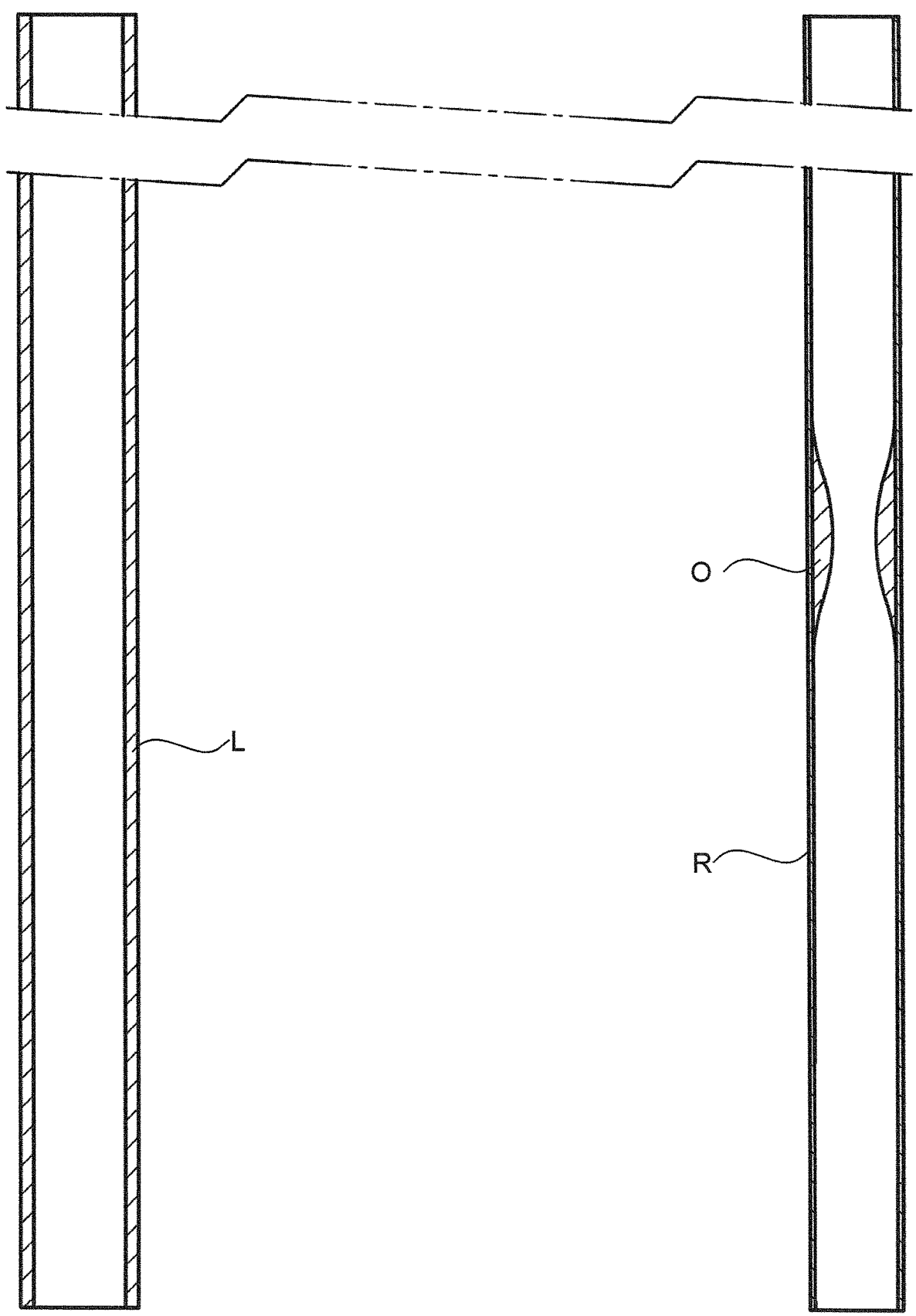

FIG. 1 schematically shows a LIMA L and a RIVA R. Within the RIVA R, a constriction or blockage O is present. This blockage shall be bypassed. A bypass of the LIMA L to the RIVA R is intended. It is emphasized that the inventive intervention kit could also be used to bypass other body vessels and to connect other vessels of the patient.

The inventive intervention kit comprises several items, especially catheters, guide wires and needles. The out-of-body handling tools of the inventive intervention kit, which are used to handle the items introduced into the body vessels, are not shown. They are well known in the state of the art and therefore not described herein in detail.

Figure 2:
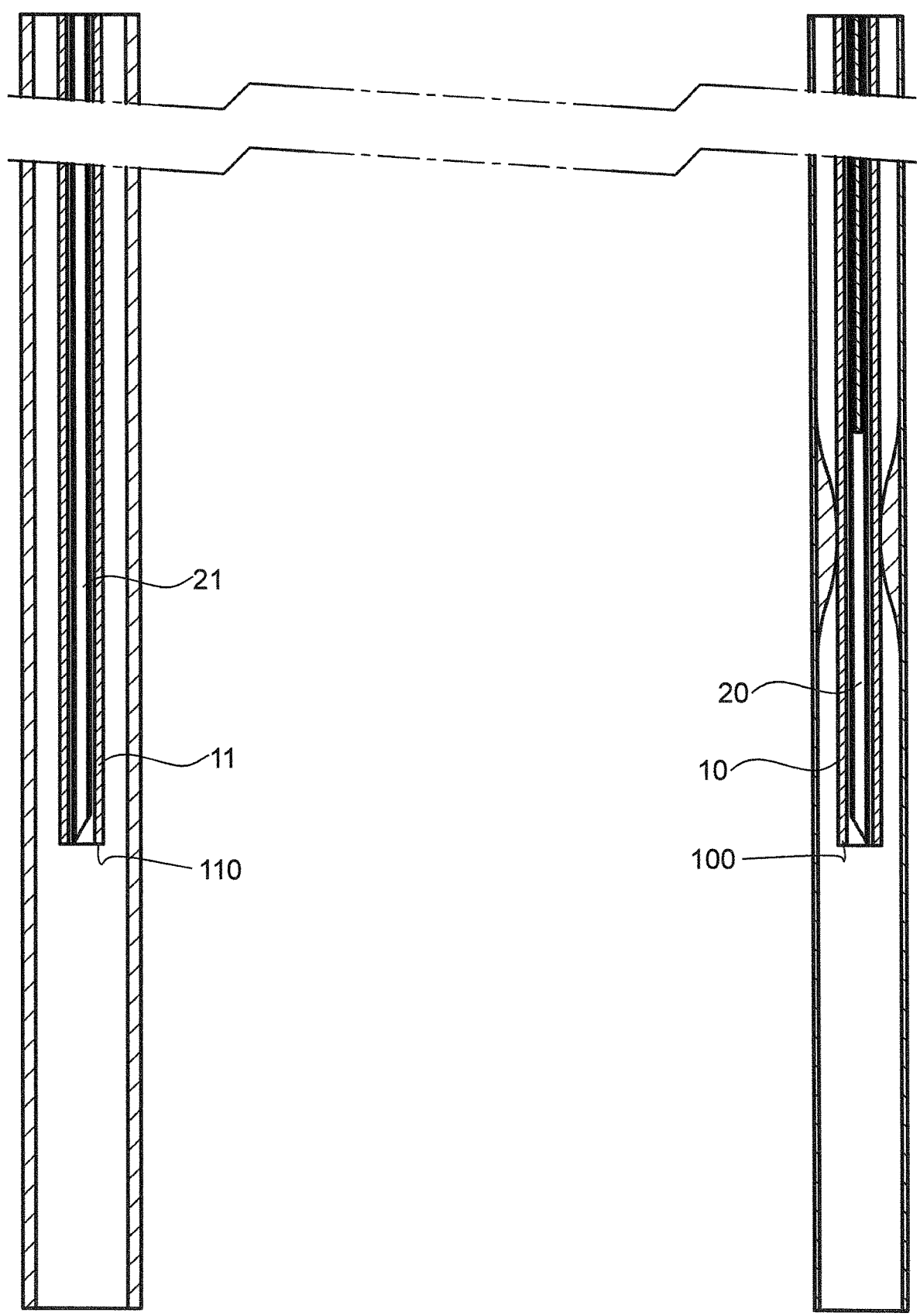
FIGS. 2 to 23 the intervention kit according to a first embodiment of the invention in use, when placing a bypass between LIMA and RIVA.

The items of the intervention kit supposed to be introduced into the human body are hereafter described in detail in the chronological order of their use:

As shown in FIG. 2, a first catheter 10 with a first needle 20 therein is introduced into the RIVA R and moved past a blockage O. A second catheter 11 is with a second needle 21 therein is introduced into the LIMA L and moved along the vessel. The first catheter 10 can be brought in first or the second catheter 11 can be first.

Figure 3:
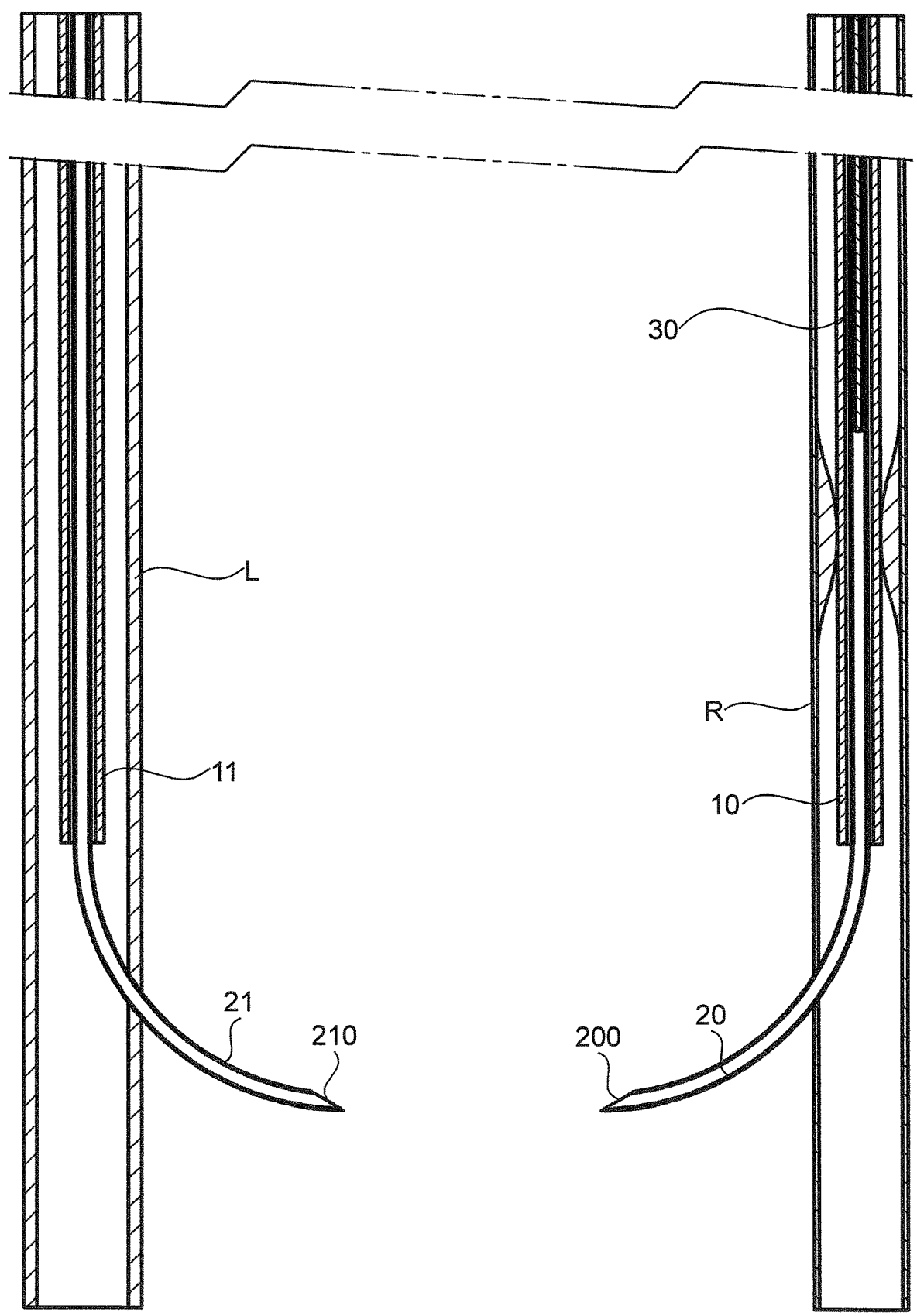

The first and second catheters 10, 11 are moved within the RIVA and LIMA respectively until their first and second end 100, 110 reach a specific place. The position of the two ends 100, 110 can for example be detected by X-ray, the two ends 100, 110 comprising or being formed as X-ray markers. When this place is reached, the first and second needles 20, 21 are forwarded out of the respective catheters 10, 11. The ends of the needles 20, 21 can be curved as shown in FIG. 3. One or both of them can be straight as well. When they are curved, the two needles can be identically curved and can have the same diameter and cutting edge 200, 210. They can also differ from each other.

The first needle 20 then cuts with its first cutting edge 200 a first aperture in the RIVA and the second needle 21 cuts with its second cutting edge 210 a second aperture in the LIMA. The two apertures lay preferably adjacent to each other so that the graft or bypass element can be quite short in length.

In a next step, shown in FIG. 3, the first and second needles 20, 21 are moved through the newly made apertures to the outside of the respective vessels L, R and towards each other. At least the first needle is hollow throughout its whole length, comprising a central lumen which opens to the outside at the first cutting edge 200. Preferably, both needles 20, 21 are hollow with a central lumen opening to the outside at the cutting edge 200, 210.

Figure 4:
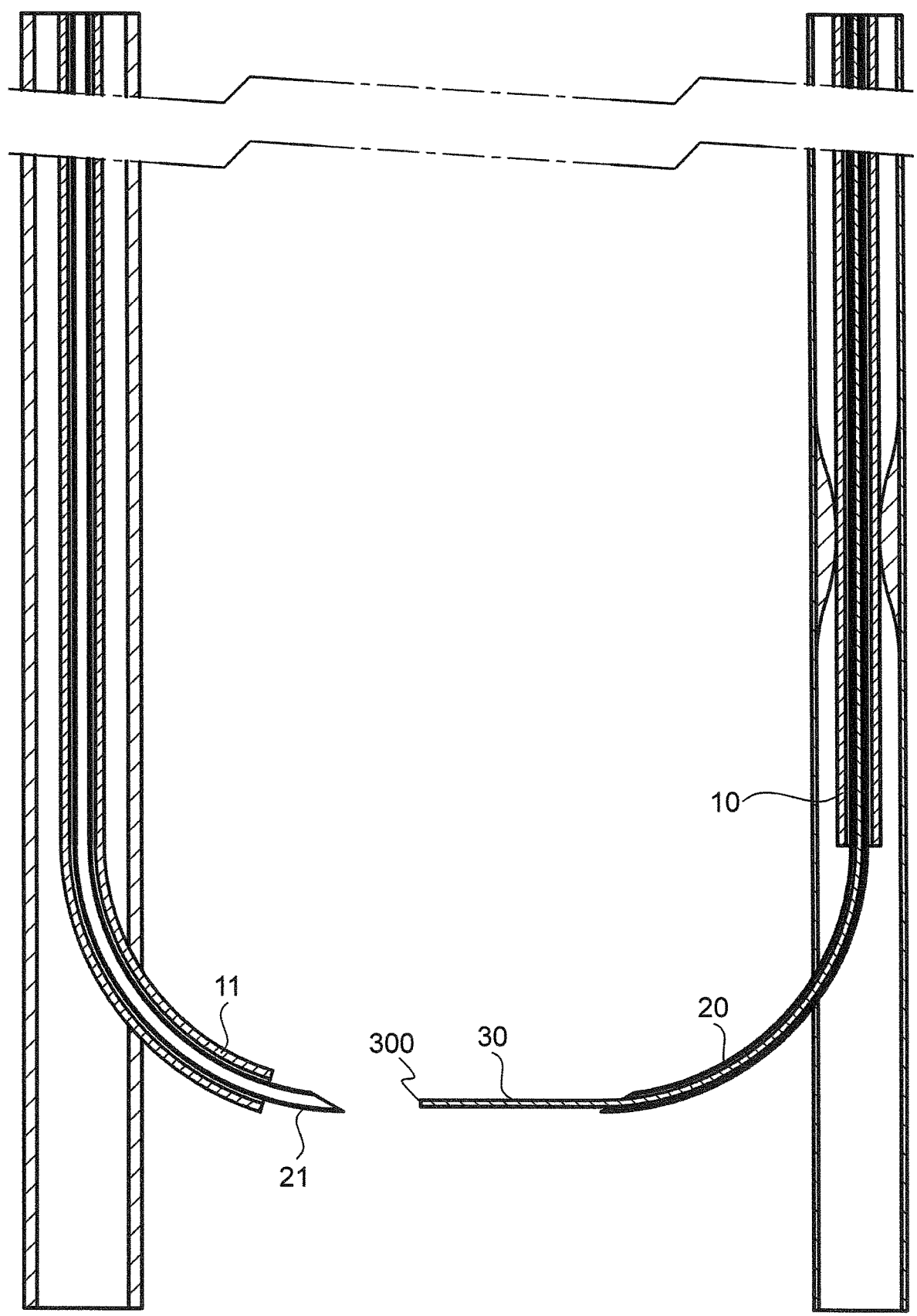

As shown in FIG. 4, a first guide wire 30, which was preferably already present within the first needle 20 (as can be seen in FIGS. 2 and 3) is moved along the lumen of the first needle 20 in direction to the first cutting edge 200. A first end region 300 of the first guide wire 30 is moved out of the opening in this cutting edge 200 in direction to the cutting edge 210 of the second needle 21. In addition the second catheter 11 is pushed over the second needle 21 through the opening made in the LIMA L.

Figure 5:
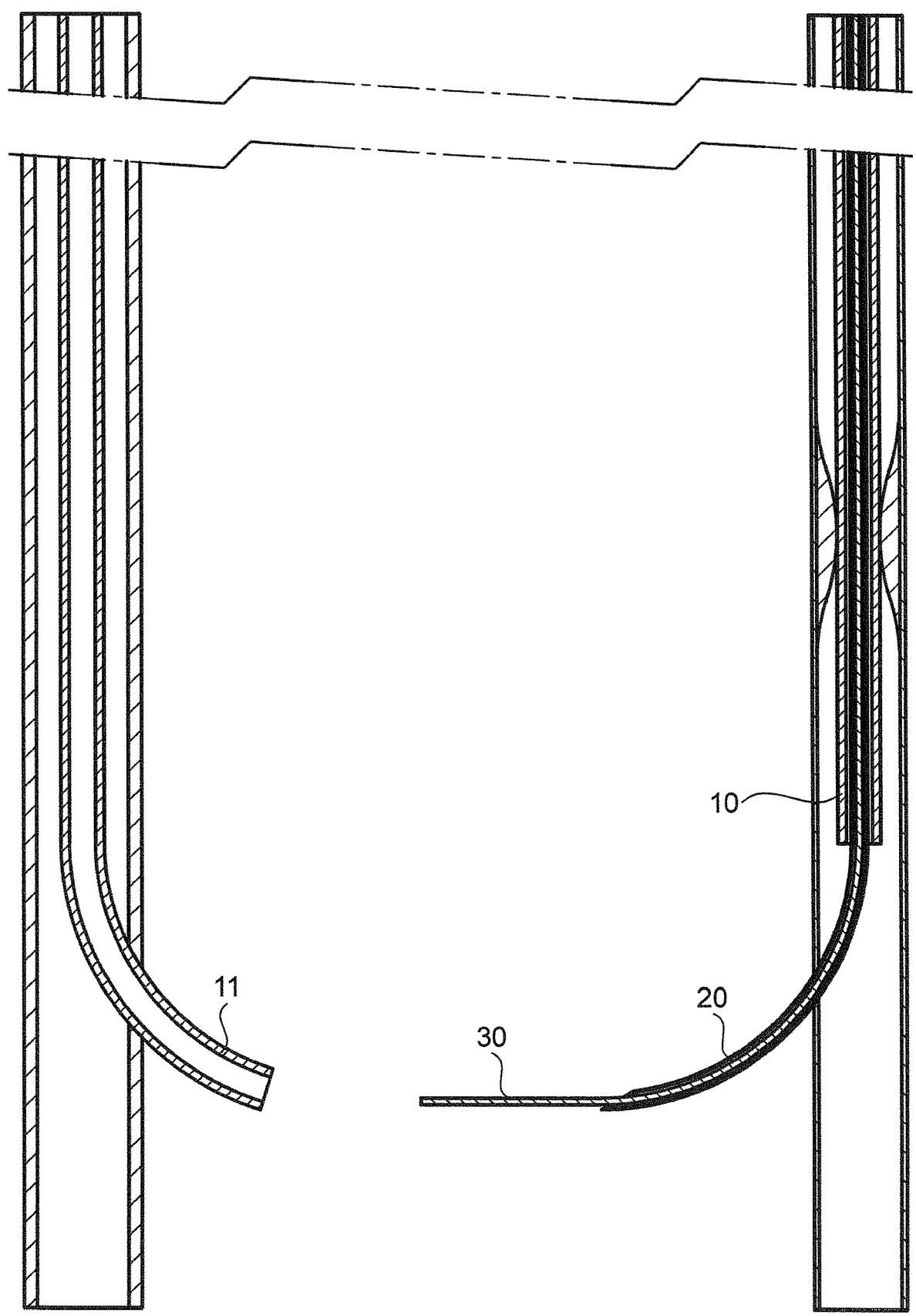

In the next step, which is shown in FIG. 5, the second needle 21 is retracted out of the second catheter 11. This step can also occur before the first end region 300 of the first guide wire 30 is moved out of the opening of the RIVA R. The step according to FIG. 6 which will be explained later can also take place before the first end region 300 is moved as mentioned above.

When the second needle 21 is removed from the second catheter 11, a second guide wire 31 is moved along the interior of the second catheter 11 until a second end of the second guide wire 31 emerges from the second end 110 of the second catheter 11.

This second guide wire 31 is preferably thicker than the first one and has less clearance within its second catheter 11 than the first guide wire 30. The second end of the second guide wire 31 is formed as a catch 310 to catch the first guide wire 30, more precisely the first end region 300. The catch can be a hook or a loop. In this embodiment, it is a loop, in particular a lasso. This can be seen in FIG. 7.

The first end region 300 and the catch 310 are brought together such that the lasso 310 catches the first end region 300. This situation is show in FIGS. 8 and 9.

Figure 10:
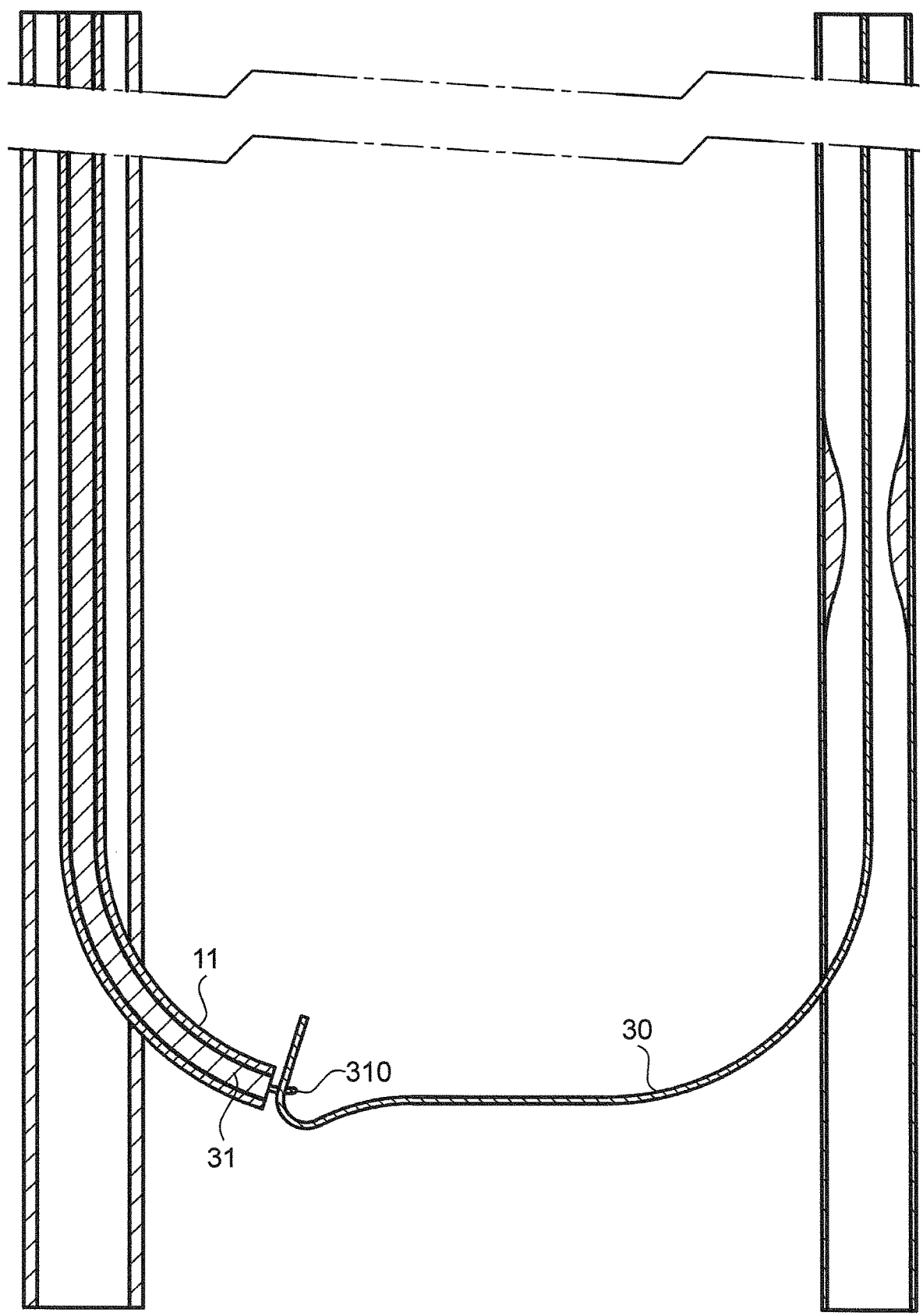

When the first end region 300 is captured, the first catheter 10 and the needle 20 are removed out of the RIVA R, leaving the first guide wire 30 in place, as shown in FIG. 10.

Figure 11:
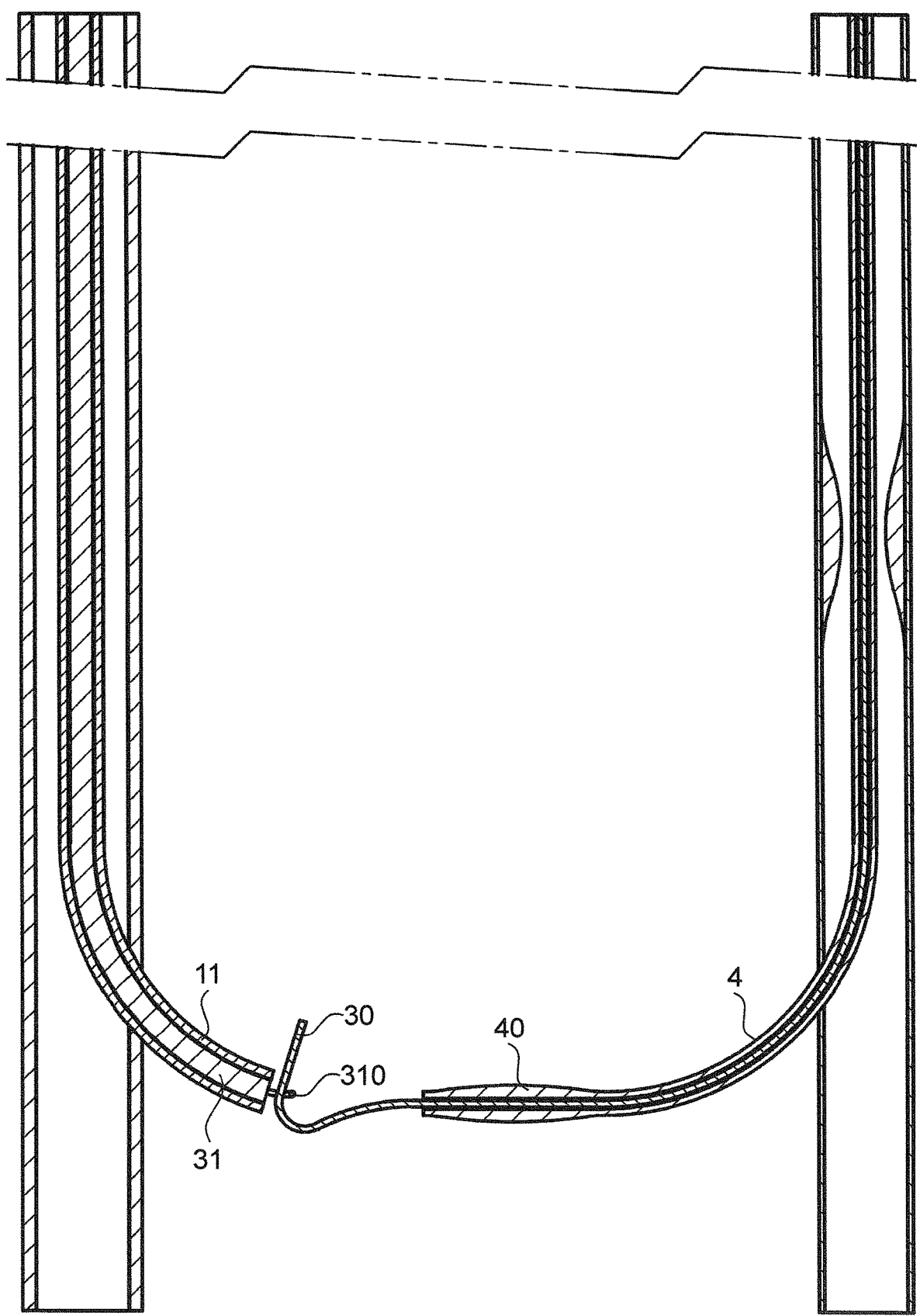

In the next step, a balloon catheter with a balloon 40 at its first end and a tail 4 following the balloon is slipped over the first guide wire 30, so that the balloon 40 and the tail 4 encompass the first guide wire 30. The balloon 40 with the tail 4 following the balloon 40 is moved along the first guide wire 30 out of the first puncture or aperture of the RIVA, as shown in FIG. 11. The balloon 40 and its tail 4 can preferably move relative to the first guide wire 30.

Figure 12:
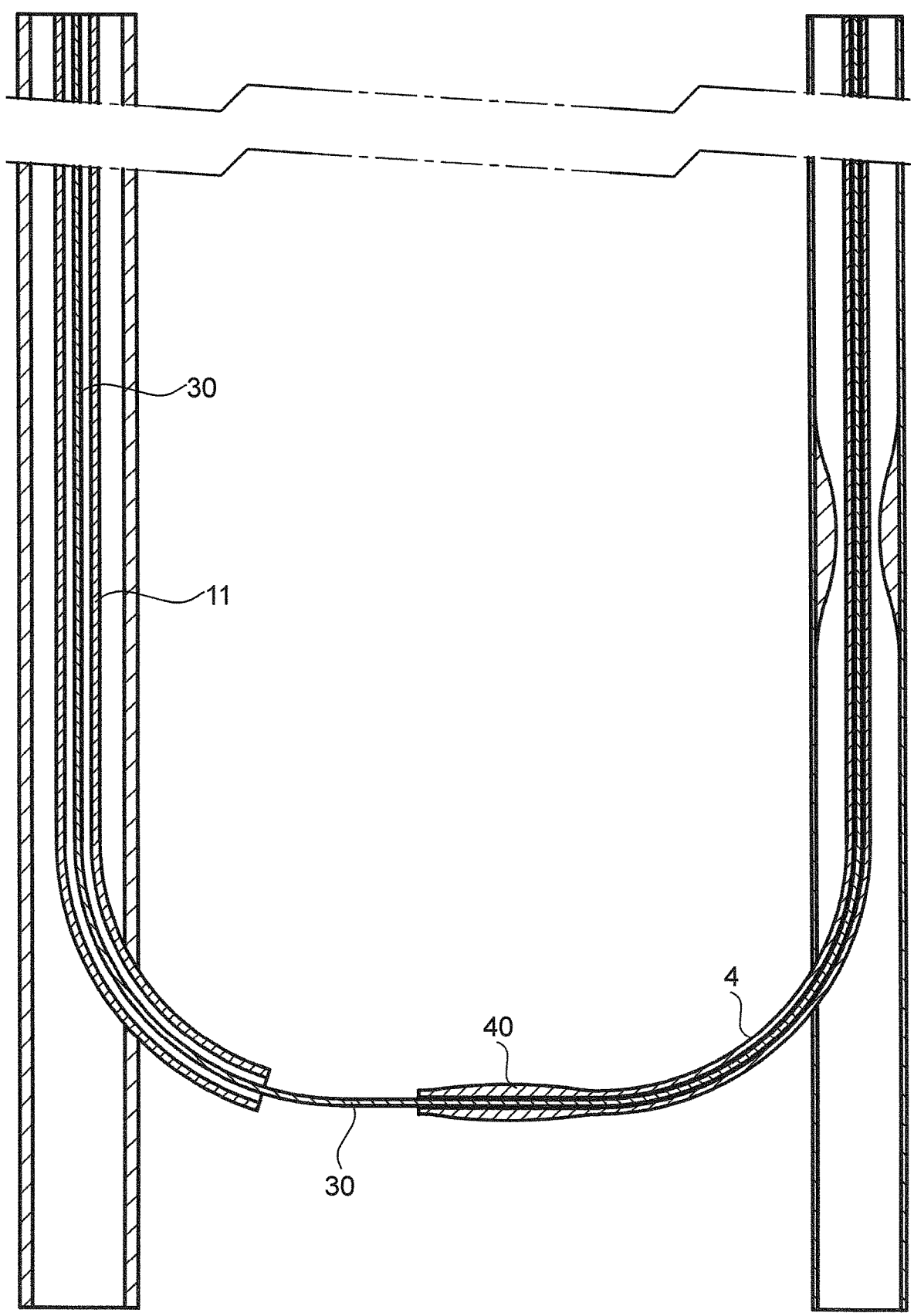

In the next step according to FIG. 12, the second guide wire 31 is retracted through the second catheter 11 and out of the LIMA L. The first guide wire 30 is pulled to follow the second guide wire 31 into the second catheter 11. The first guide wire 30 can additionally or alternatively be pushed to enter the LIMA L, by applying a pressure on the RIVA side of the first guide wire 30.

Figure 13:
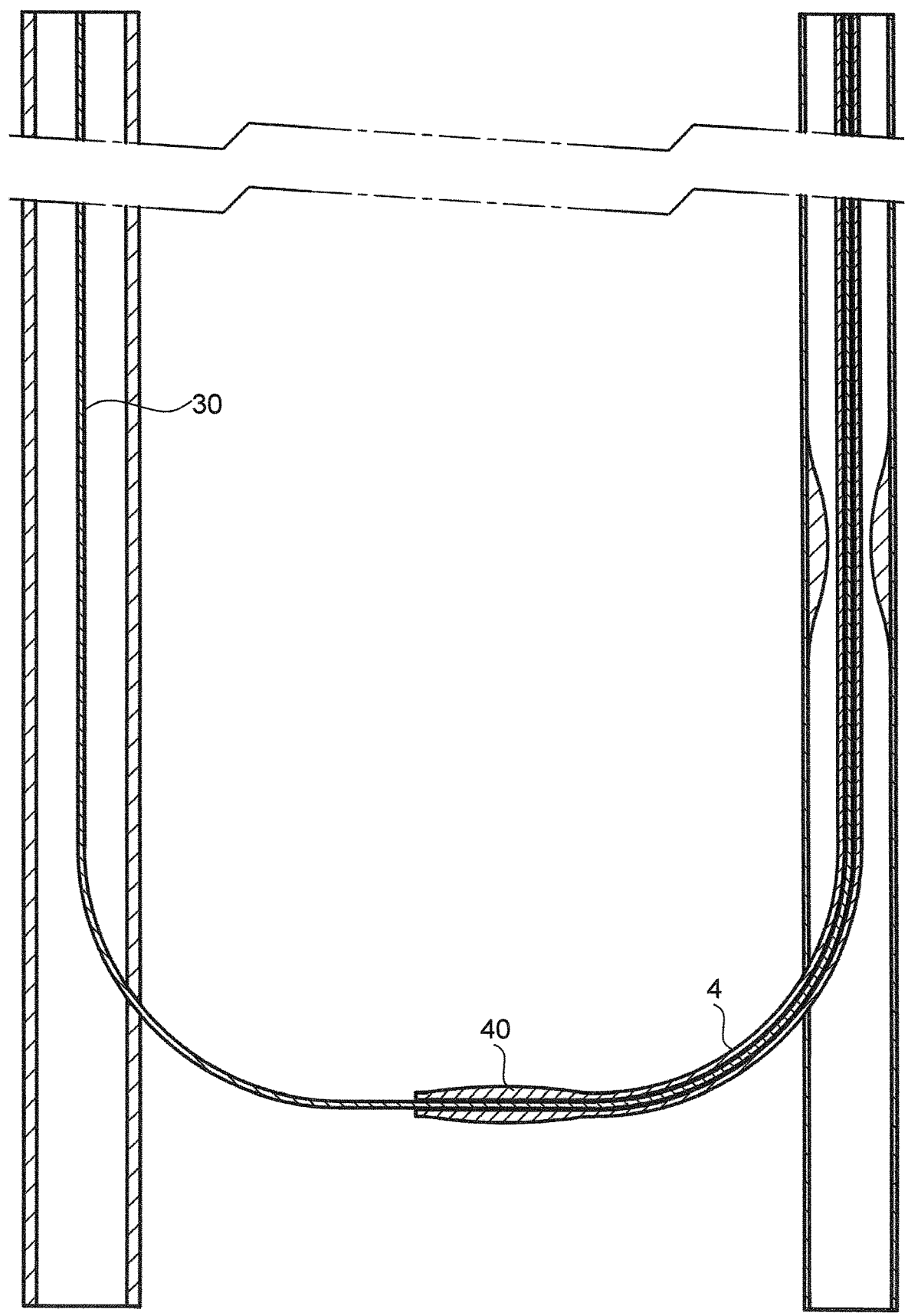

When the first end region 300 has left the LIMA L and the body (i.e. the arterial system), the second catheter 11 can be removed from the LIMA L and removed from the patient body. There is only the first guide wire 30 and the balloon 40 with its tail 4 left, as shown in FIG. 13. The first guide wire 30 is now extending from the outside of the patient body through the RIVA R to and through the LIMA L to the outside of the body again.

Figure 14:
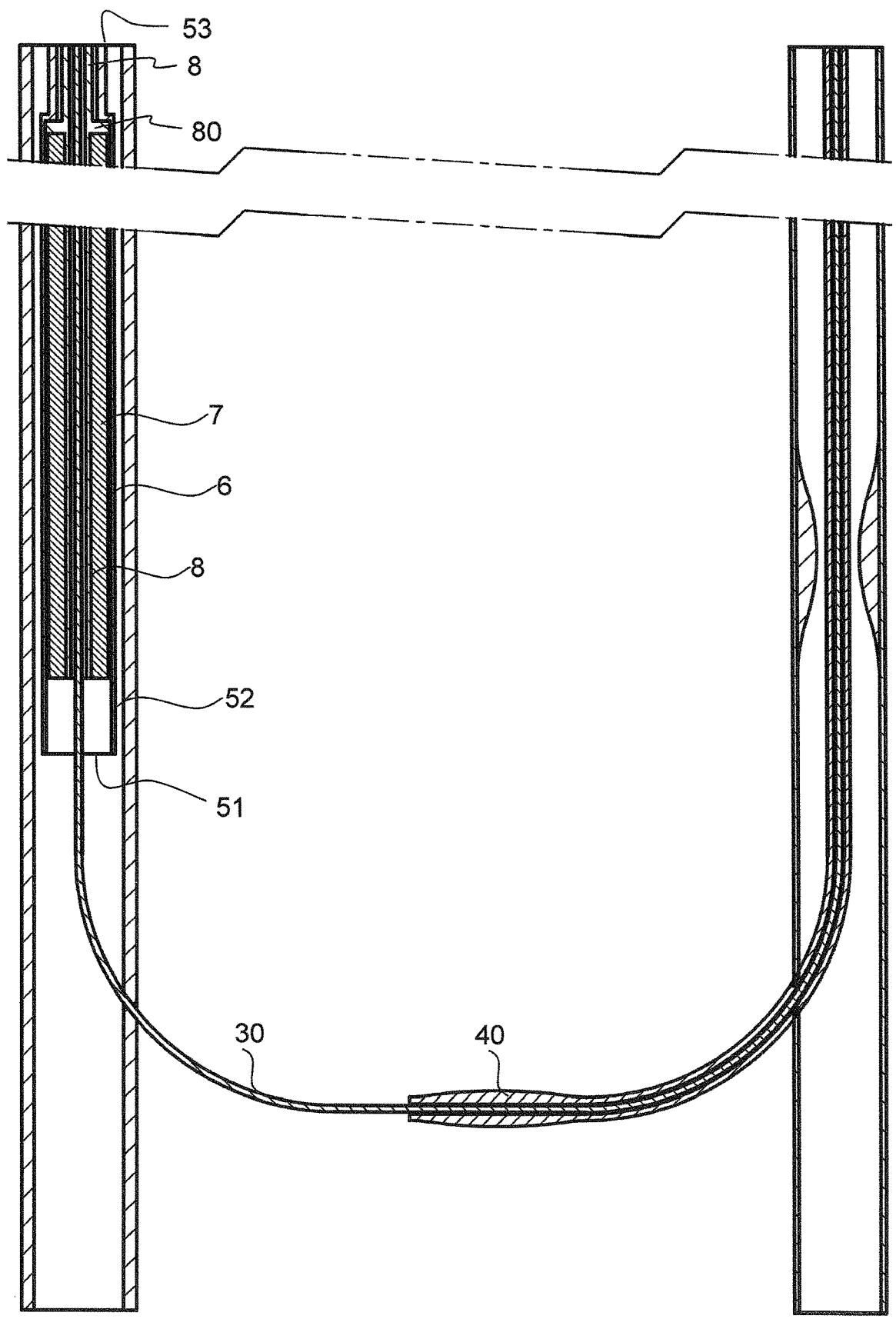

From the LIMA-side, a bypass element delivery system 52, 53, 8 holding a bypass element 6, 7 is introduced along the first guide wire 30 (see FIG. 14). The bypass element 6, 7, is a graft, a stent or a combination thereof. The graft is preferably an autograft, an isograft, an allograft or a xenograft or made of an artificial material, such as PTFE. Grafts and stents are known and are therefore not described in detail herein.

In this embodiment, the stent 6 surrounds the graft 7 approximately along their whole length, i.e. they have preferably the same length. The delivery system comprises a delivery system catheter 53 and a delivery system casing 52. The catheter 53 and the casing 52 are fixed to each other or they are made of one single piece. The casing 52 forms a capsule at the front end of the catheter 53. The catheter 53 therefore forms a small tail following the capsule and it extends until the outside of the LIMA L. In the capsule the stent 6 and graft 7 are radially compressed and hold. The capsule comprises preferably a connecting end 51 directed to the puncture of the LIMA L.

Within the delivery system catheter 53 an inner catheter 8 extends. The catheter 8 can for example end at the plunger 80 or it can extend further. The stent 6 and graft 7 are arranged within the casing 52. The inner catheter 8 comprises a plunger 80 arranged in the end of the capsule, this end being distant to the connecting end of the casing 52. This plunger 80 abuts on one side the stent 6 and/or the graft 7 and on an opposite side a stop collar 50 of the casing 52. This can be seen in FIG. 15. Inner catheter 8 and plunger 80 can be made of one single piece or being connected to each other.

Figure 15:
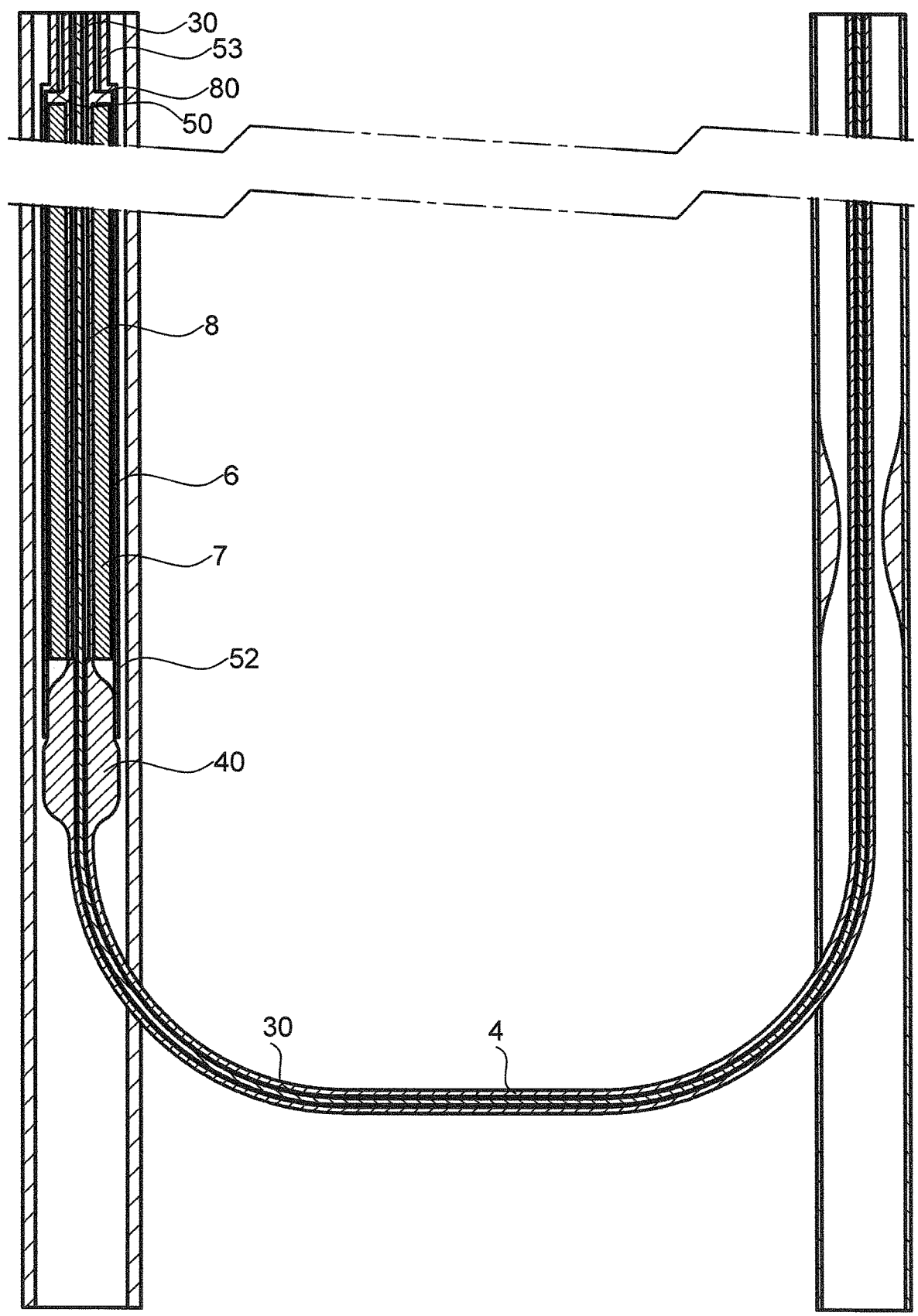

As can also be seen in FIG. 15, the balloon 40 and its tail 4 are moved through the second aperture in the LIMA L to the casing 52 and into its connecting end. There, the balloon 40 is inflated by injecting fluid from the outside through the tail 4 into the balloon 40. The balloon 40 is inflated until it captures the casing 52 and holds it tight.

The balloon 40 can also be moved, in absence of the delivery system at the place as shown in the figure, further along the LIMA L to another place to catch the casing 52. The balloon 40 can even be brought to the proximal end of the LIMA L and to the outside of the patient in order to catch the casing 52 at the outside.

Figure 16:
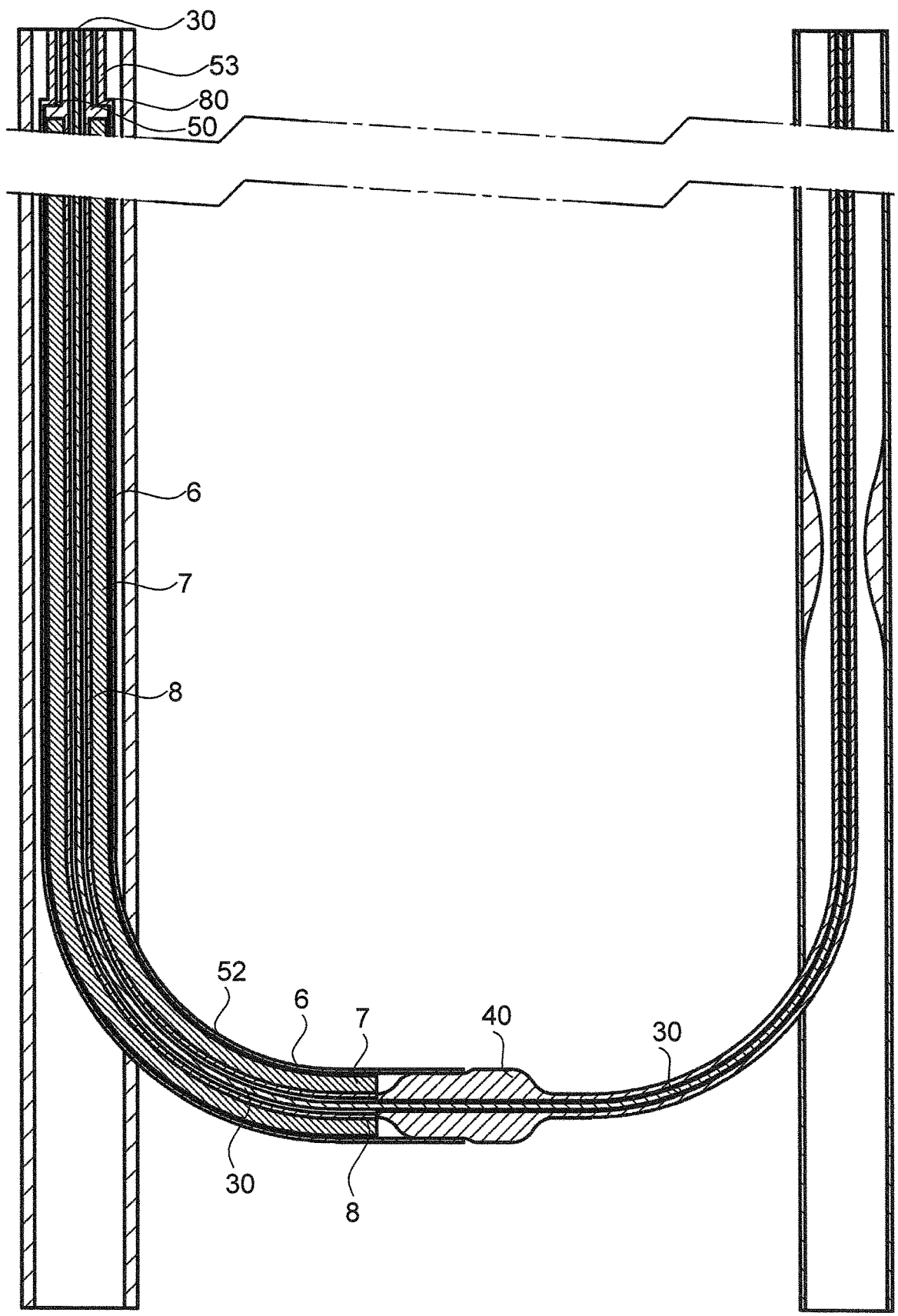
Figure 17:
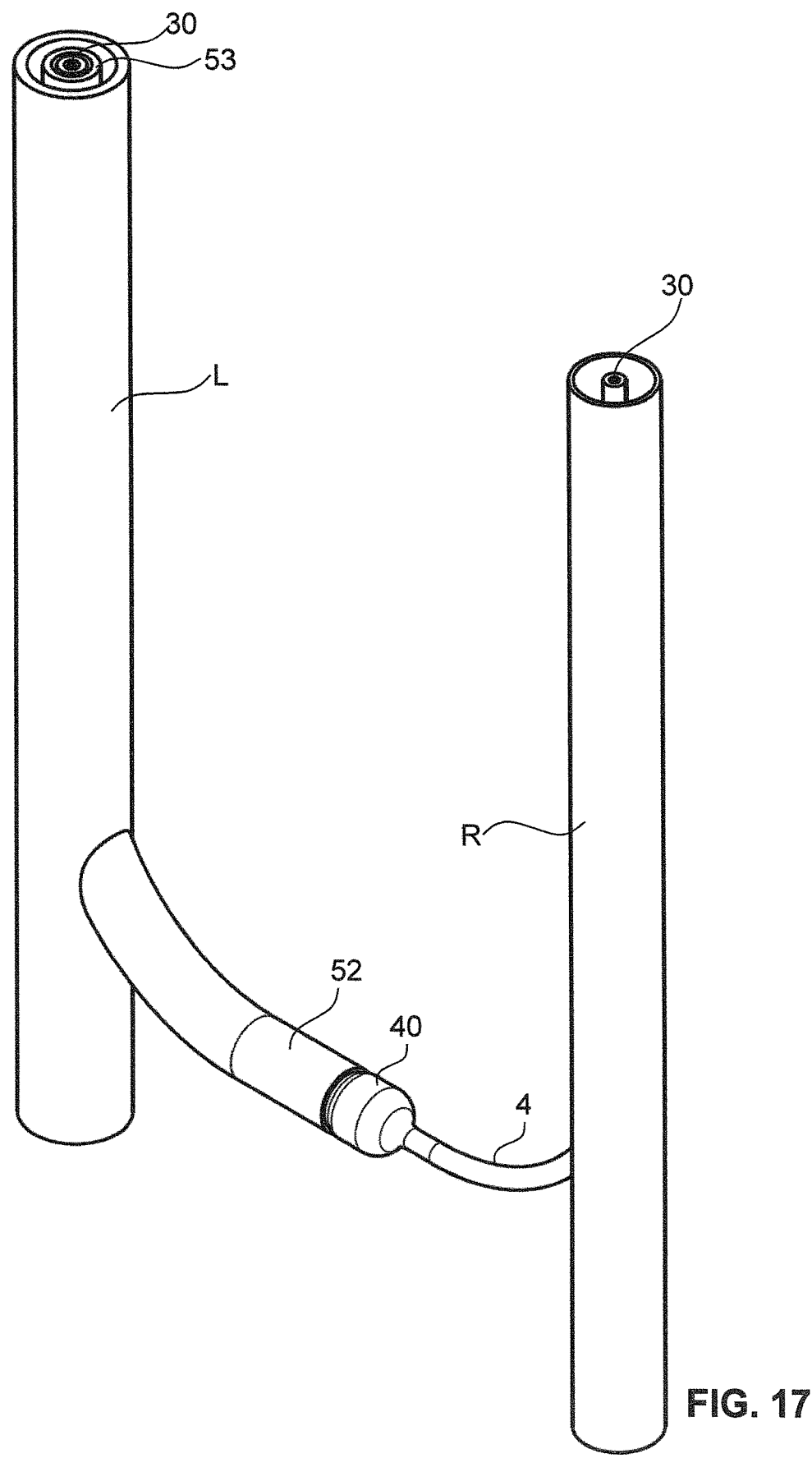
Figure 18:
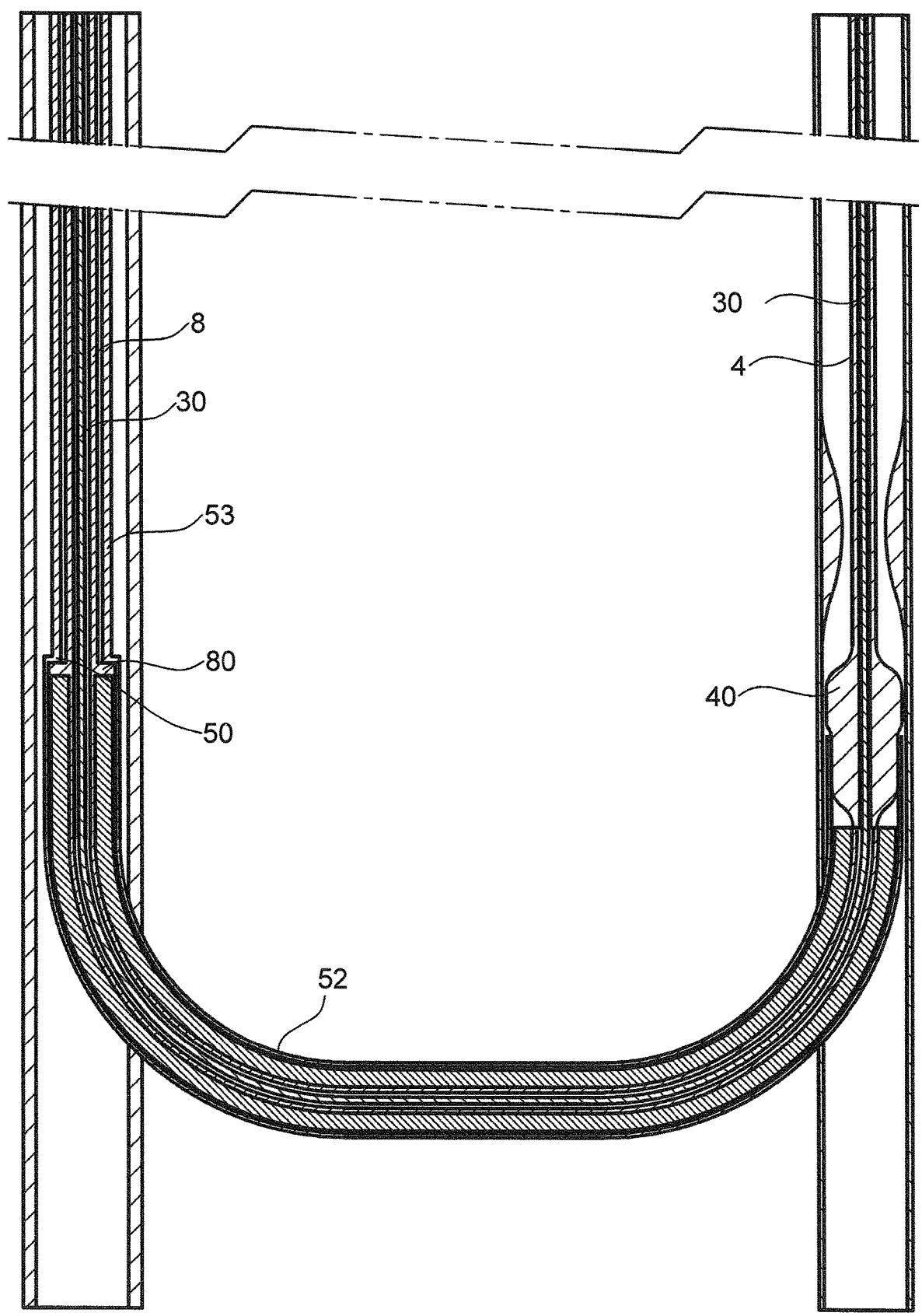
Figure 19:
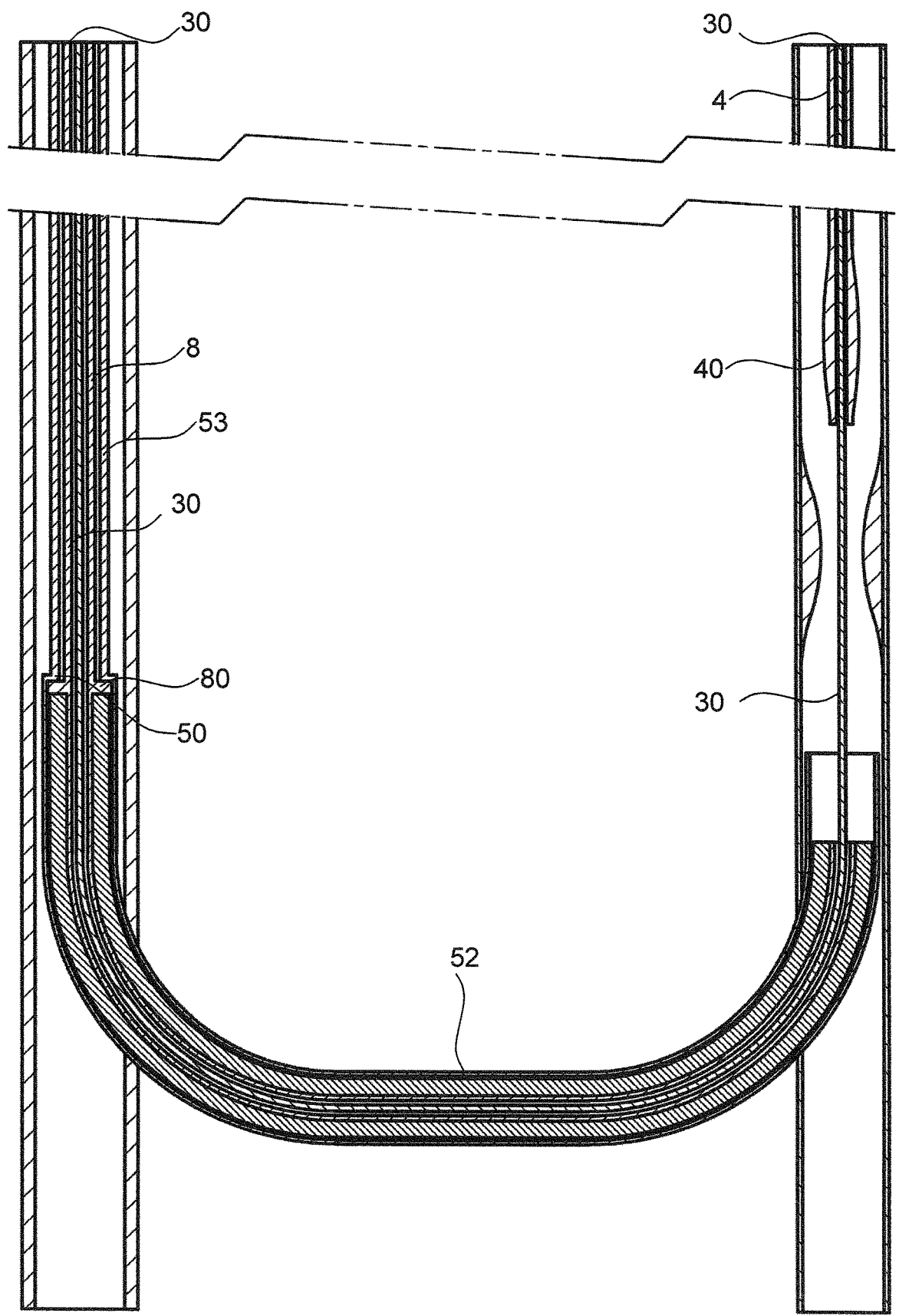

Having the casing 52 captured, the balloon 40 is retracted by its tail 4 in direction to the RIVA R, taking the delivery system 52, 53, 8 and the bypass element 6, 7 with it. In FIGS. 16 and 17 the delivery system 52, 53, 8 has already passed the second puncture in the LIMA L and in FIG. 18 it has entered together with the balloon 40 the RIVA R, using therefore the first puncture in the RIVA R.

The balloon 40 is then deflated and removed at least behind the blockage O. Preferably it is hold in place shortly behind the blockage O in case it is needed to rearrange the casing 52. The steps shown in FIGS. 15 to 19 can be performed in a minimum of time, therefore closing the RIVA R and LIMA L as short as possible.

Figure 20:
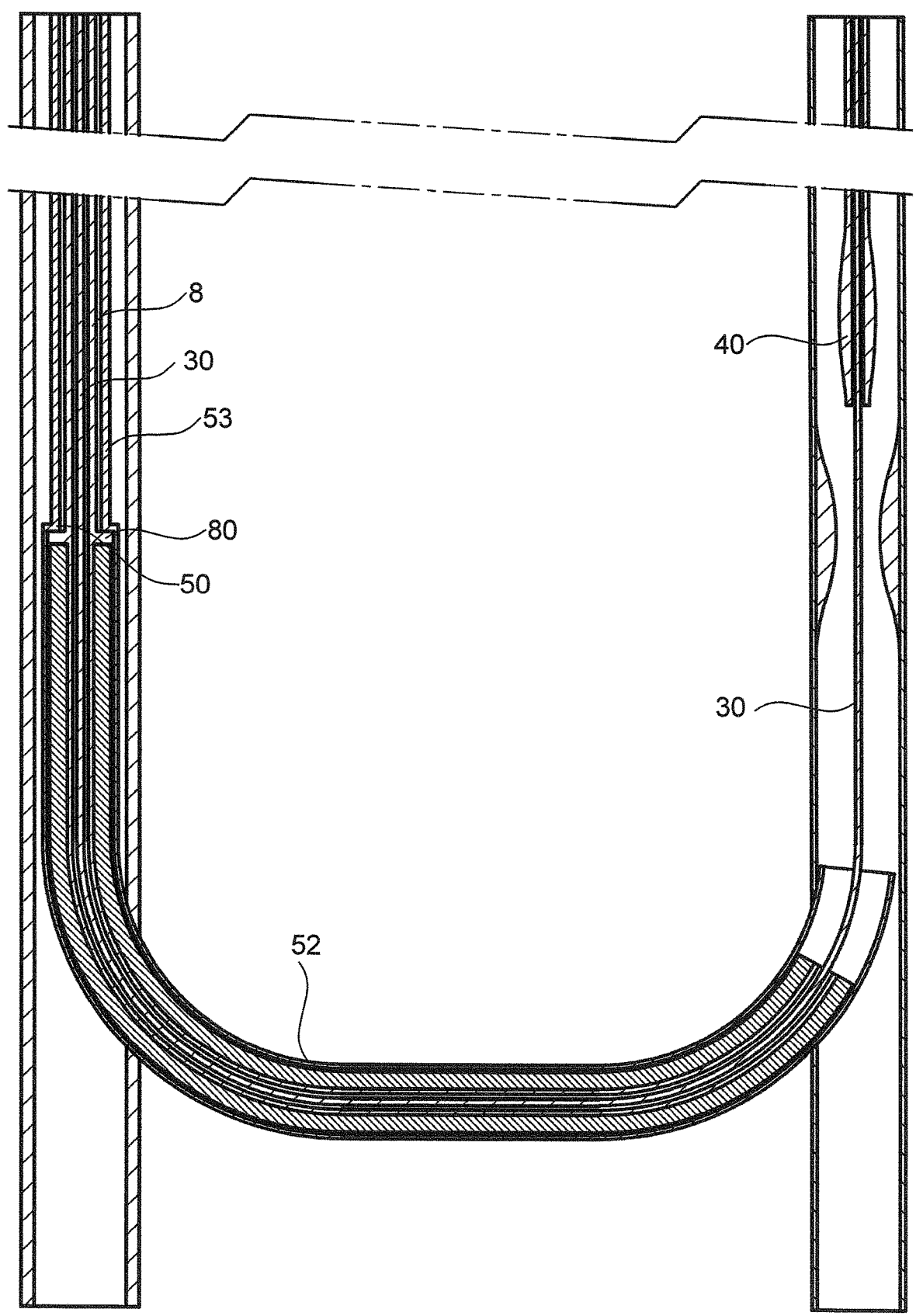

The bypass element 6, 7, is now placed in the correct position by retracting the delivery catheter 53 with the casing 52 again. This is shown in FIG. 20. The placement can once again be monitored in well-known ways, such as by using X-ray markers.

Figure 21:
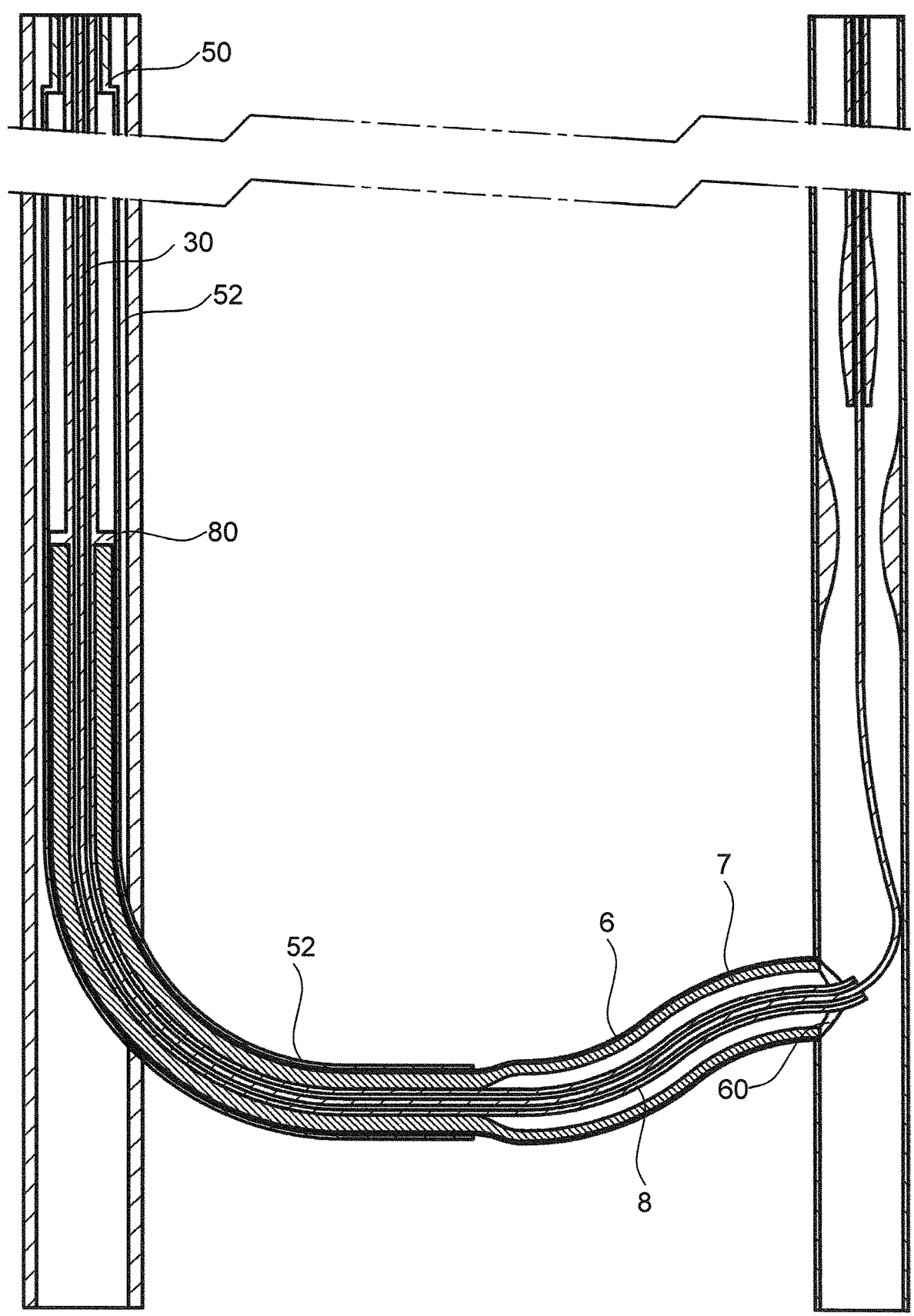

When the bypass element 6, 7 is ideally placed, the delivery catheter 53 with the casing 52 is retracted from the RIVA to the LIMA, as shown in FIG. 21. The inner catheter 8 remains in place and the plunger 80 keeps thereby the bypass element 6, 7 in place. An end 60 of the bypass element 6, 7 is located within the RIVA, adjacent the inner side of the first puncture. This end 60 can comprise retaining elements to hold the bypass element in place as well. This will be described later on. In other embodiments the other end comprises retaining elements as well.

The inner catheter 8 extends preferably along the bypass element 6, 7 encompassing the first guide wire 30 along the whole length of the bypass element 6, 7.

Figure 22:
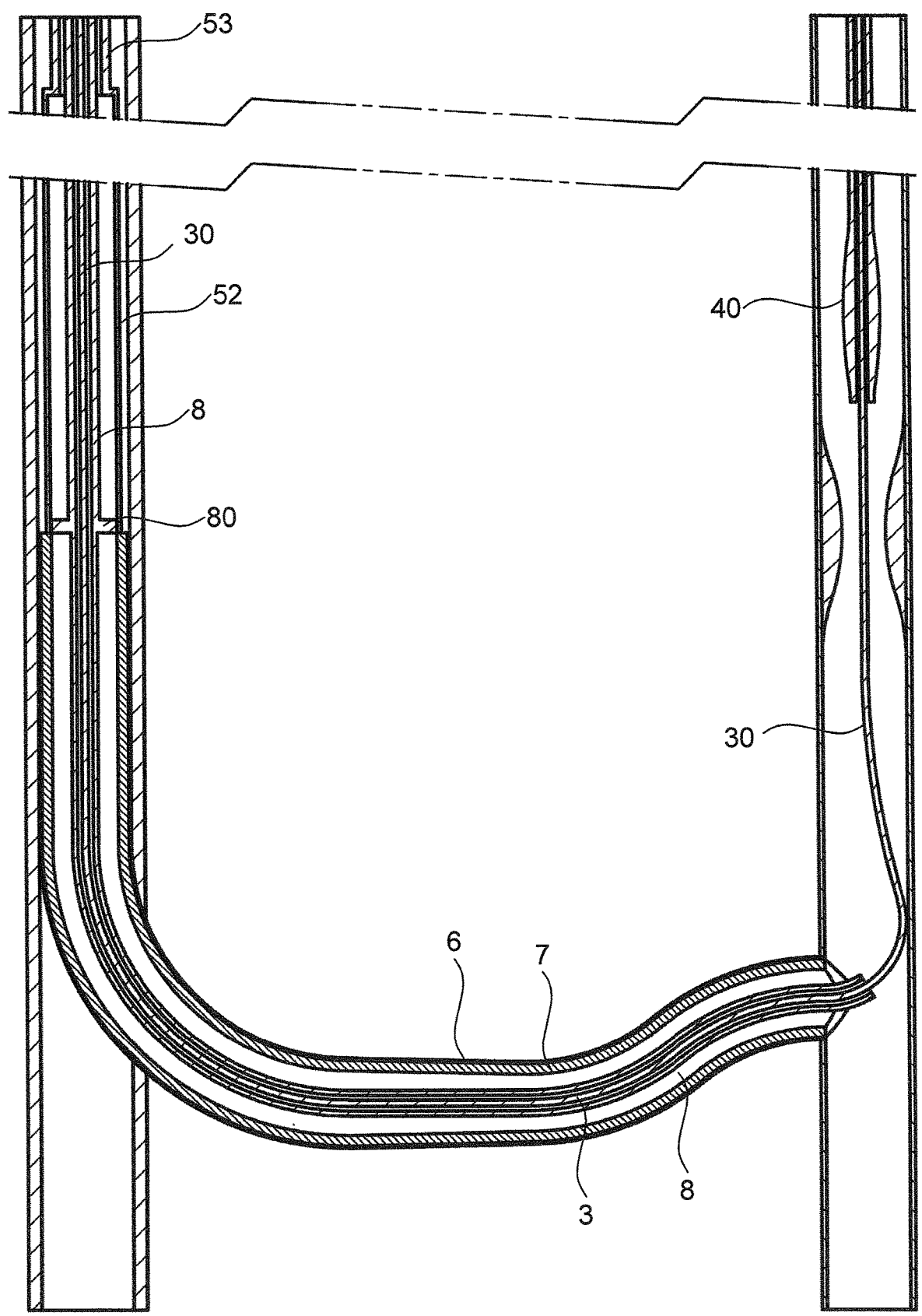
Figure 23:
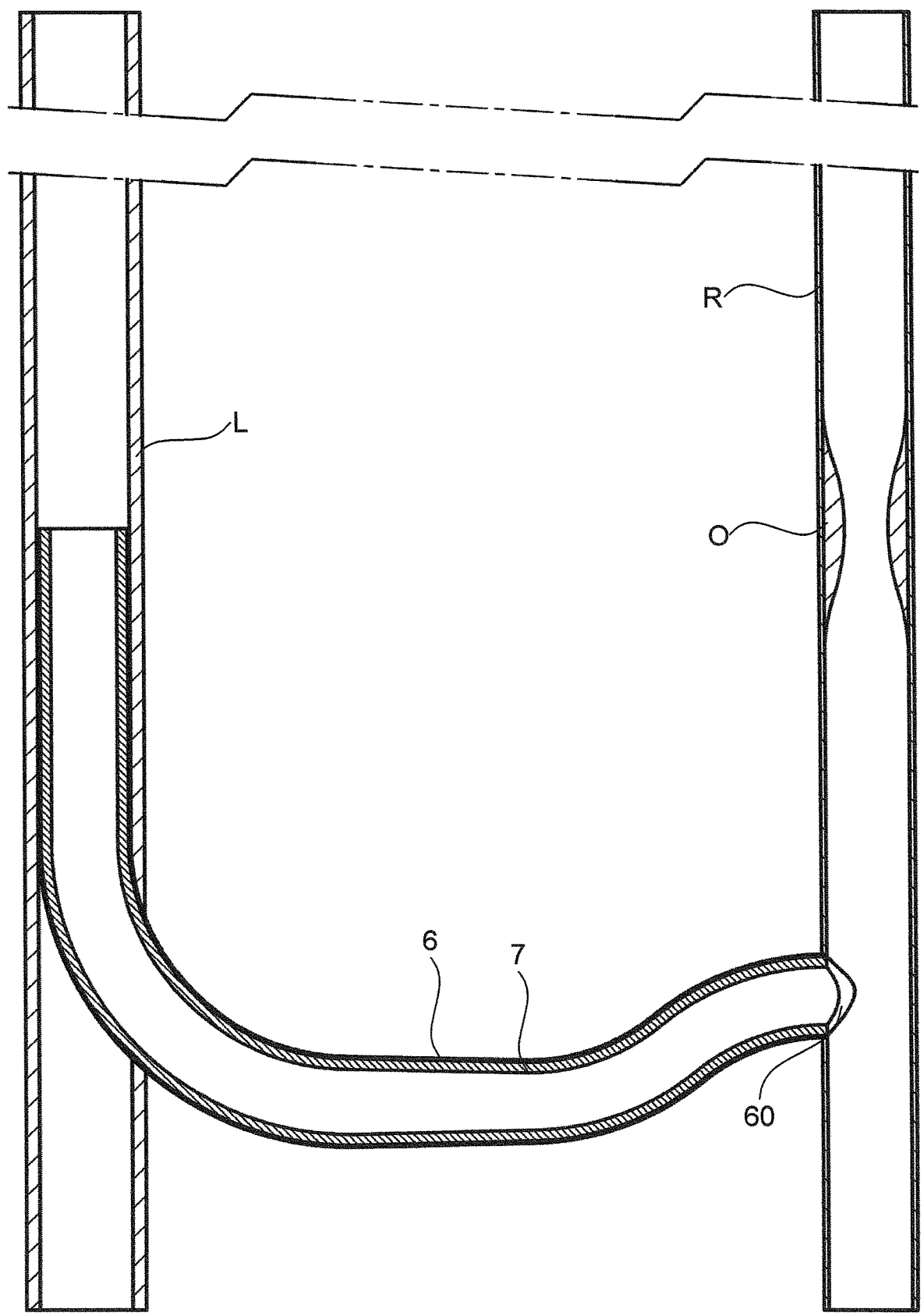

In FIG. 22, the delivery catheter 53 and the casing 52 are completely removed from the bypass element 6, 7 and have set it free. The plunger 80 still abuts one end of the bypass element 6, 7. The inner catheter 8 and the first guide wire 30 can then be removed as well. The only element remaining in the patient's body is the bypass element 6, 7 forming a connection between RIVA and LIMA, as shown in FIG. 23.

Figure 24B:
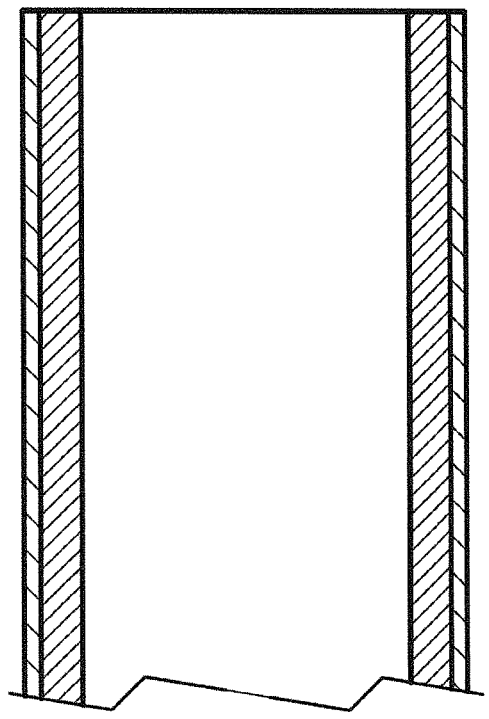
Figure 24B:
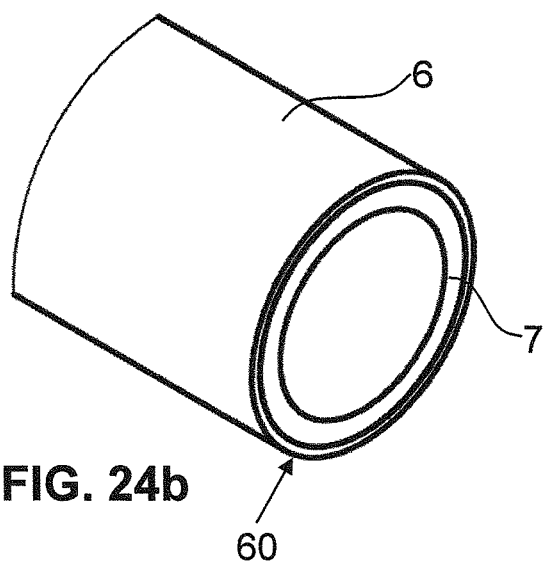
Figure 24A:
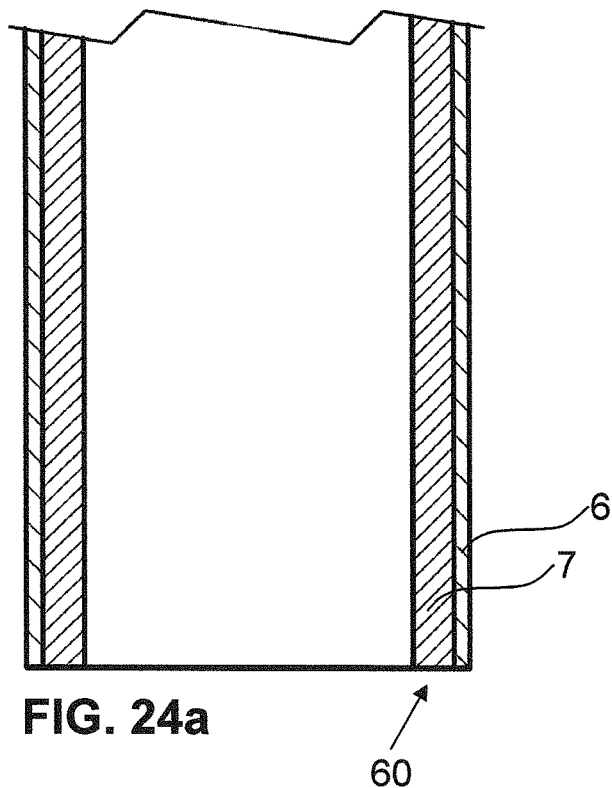
FIG. 24a a longitudinal section through an end of a bypass element in a first embodiment.

The end 60 of the bypass element 6, 7, can be planar without any retaining means as shown in FIGS. 24a and 24b.

Figure 25B:
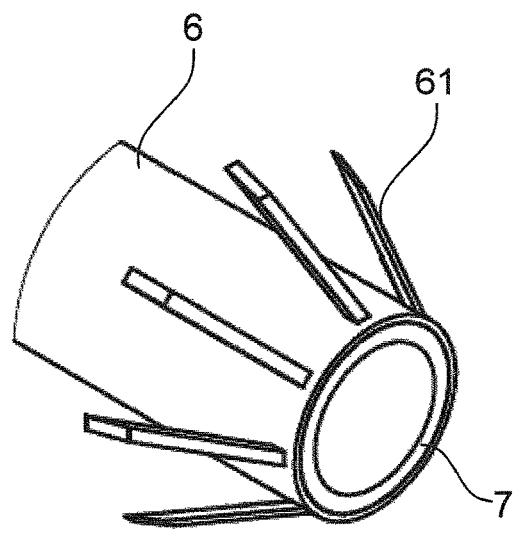
Figure 25A:
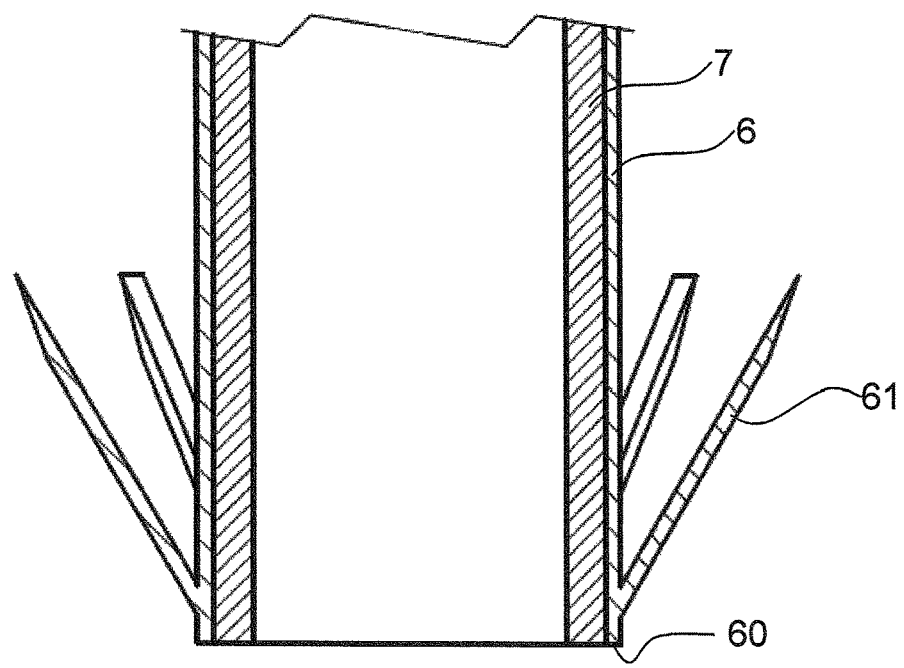
FIG. 25a a longitudinal section through an end of a bypass element in a second embodiment.

Preferably, some anchoring elements are present. In the embodiment according to FIGS. 25a and 25b, the stent 6 comprises some spikes 61. The spikes 61 are directed in an angle away from the end 60. They are arranged preferably on the circumferential outer surface of the stent 6. They are arranged preferably equidistant and on a circle parallel to the face of the end 60.

Figure 26A:
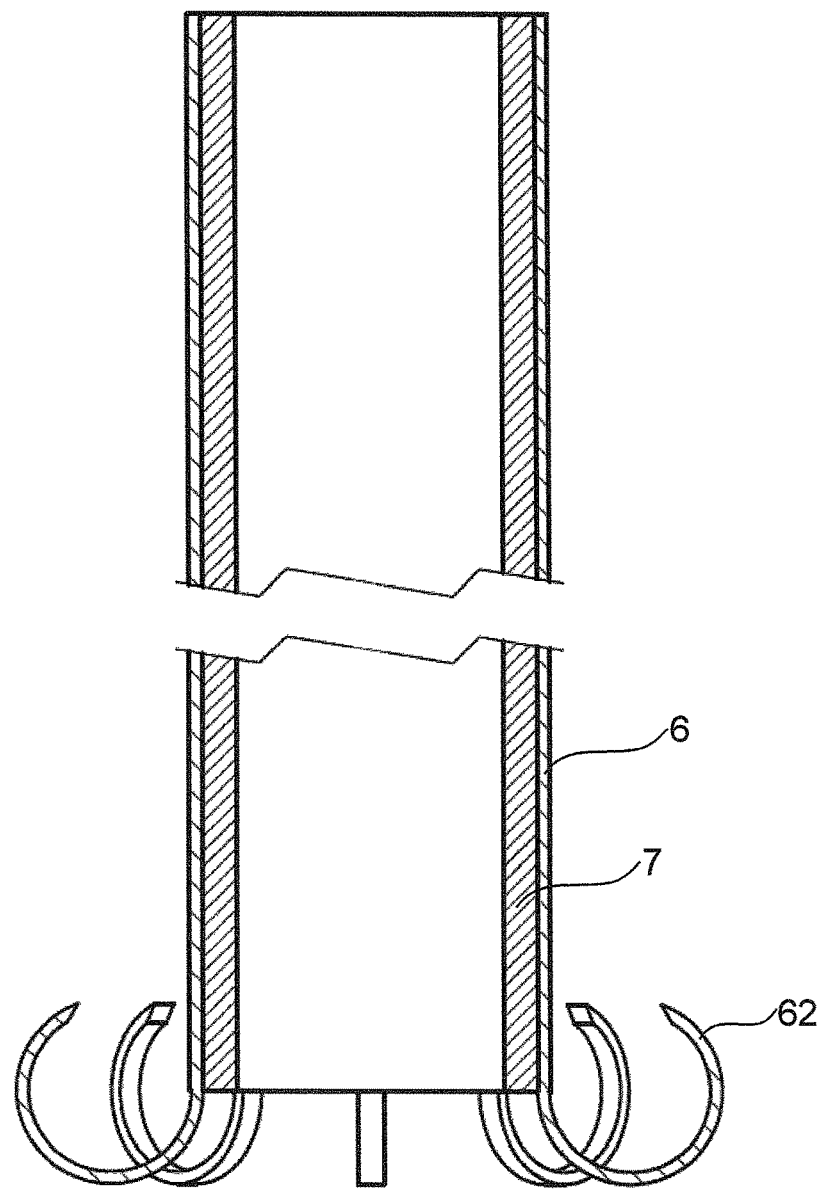
FIG. 26a a longitudinal section through an end of a bypass element in a third embodiment.
Figure 26B:
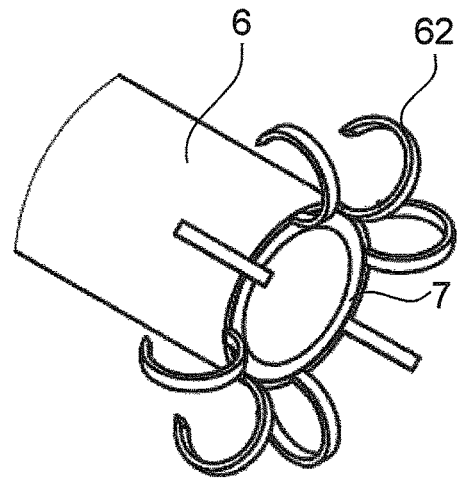
Figure 27A:
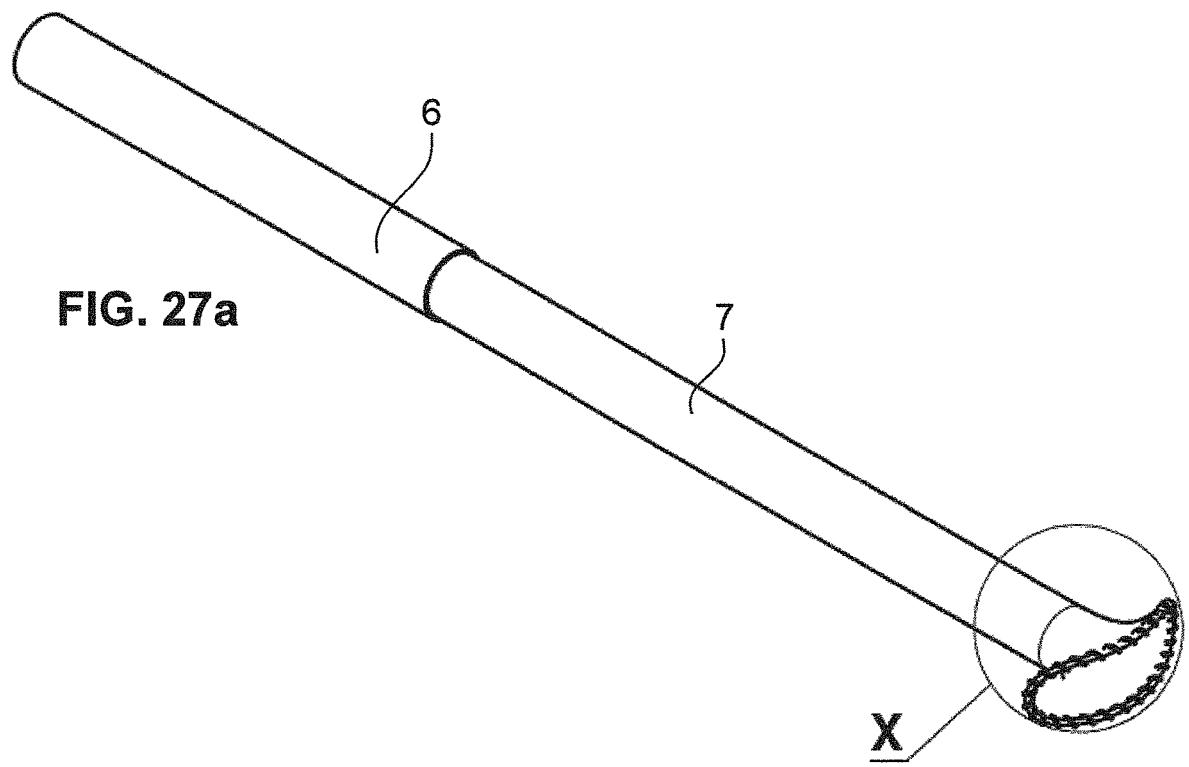
FIG. 27a a perspective view of an end of a bypass element in a fourth embodiment.
Figure 27B:
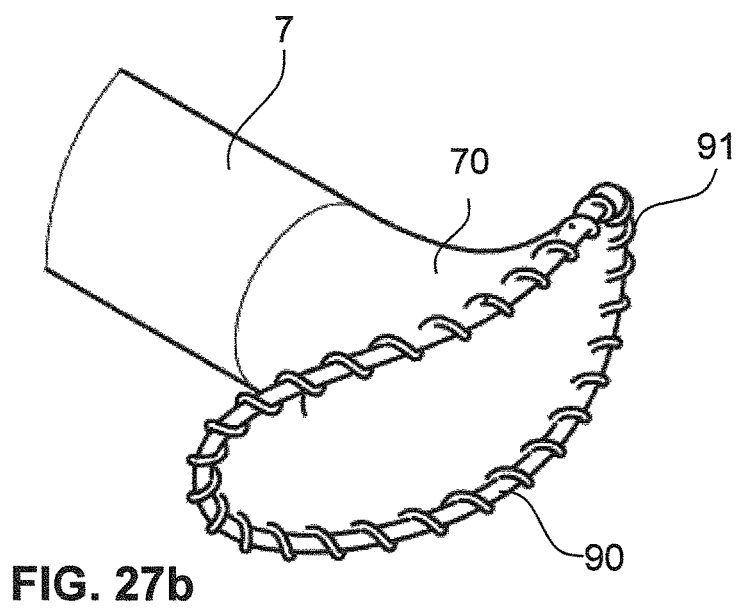
Figure 27C:
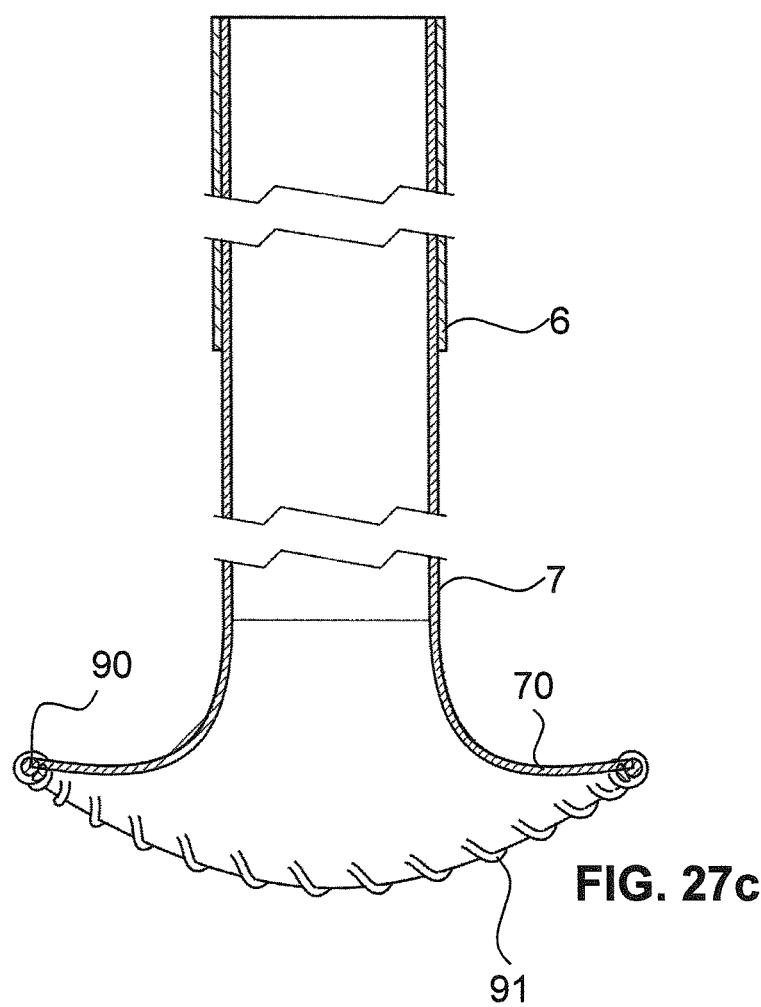
Figure 27D:
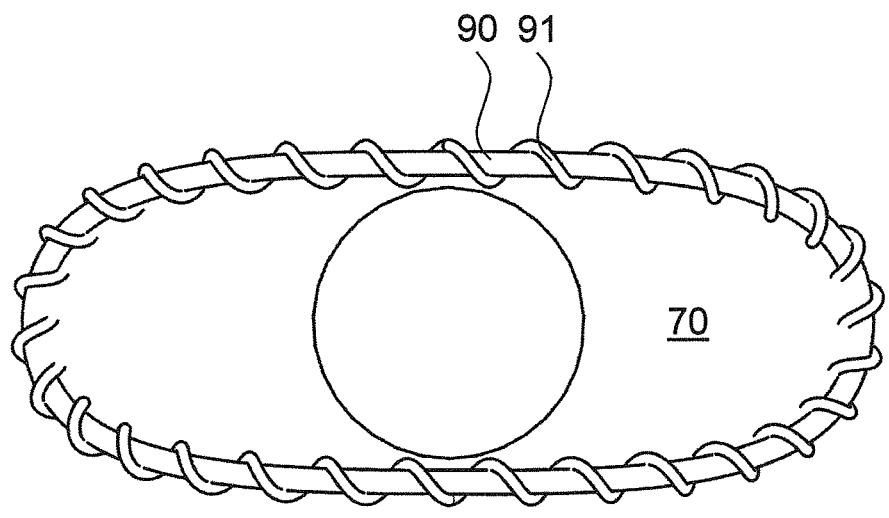

In the embodiment according to FIGS. 26a and 26b, there are hooks 62 arranged at the outer surface or the face of the end 60 of the stent. Once again, they are preferably distributed circumferentially and preferably equidistant.

In the embodiment according to FIGS. 27a to 27d, the graft 7 comprises an anchoring element. There may be a stent 6 present or not. The graft 7 preferably has an end 70 which has a widening. This widening is reinforced with a ring 90 fixed to the graft. The ring 90 can be sewed with one or more threads 91 or otherwise fixed, even without threads.

The ring 90 is preferably made of nitinol. The ring 90 is preferably flexible enough to be compressed within the capsule of the casing.

The shape of the widened end 70 and the ring 90 is such that it snuggles or clings perfectly to the inner surface of the vessel surrounding the first aperture or puncture, thereby preferably overlapping the whole puncture. The shape can be described as generally oval head being inclined with respect of a middle longitudinal axis of the graft 7. The widened end 70 can however also be round. Other shapes and angles of this end 70 are possible as well.

The delivery system 52, 53, 8 is just one possible example which can be used in the inventive intervention kit. The delivery system 52, 53, 8 depends on the bypass element to be used. The delivery system can therefore also be made different from the one described therein, especially other delivery systems known in the state of the art can be used as well.

Figure 28A:
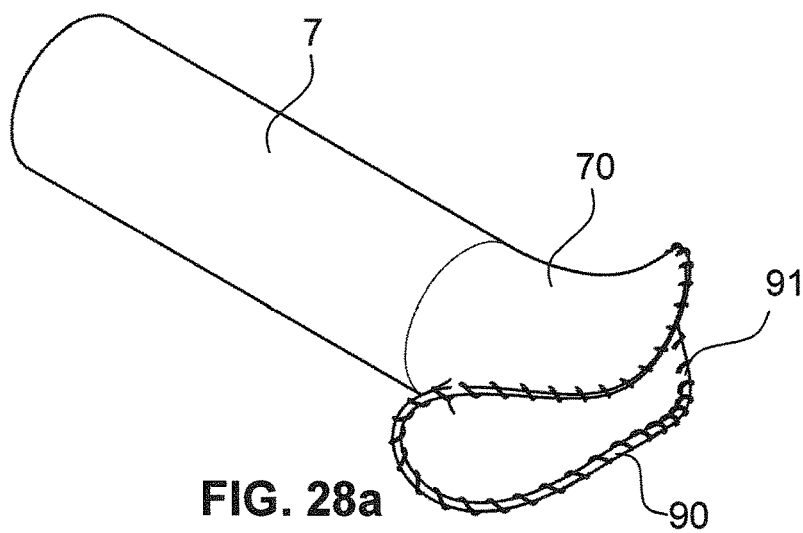
FIG. 28a a perspective view of an end of a bypass element in a fifth embodiment.
Figure 28B:
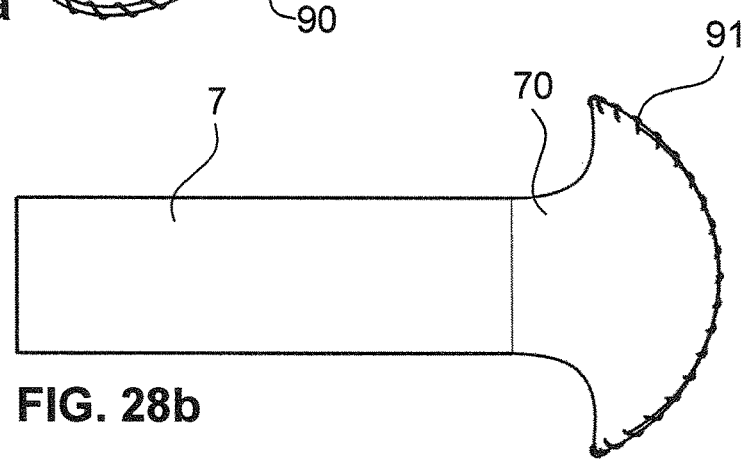
Figure 28C:
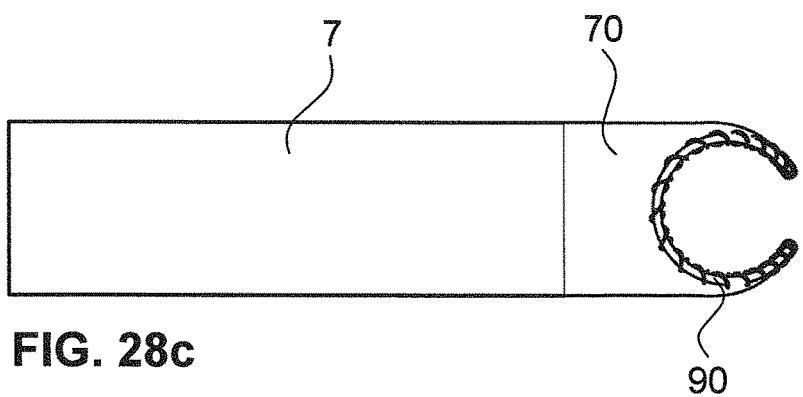
Figure 28D:
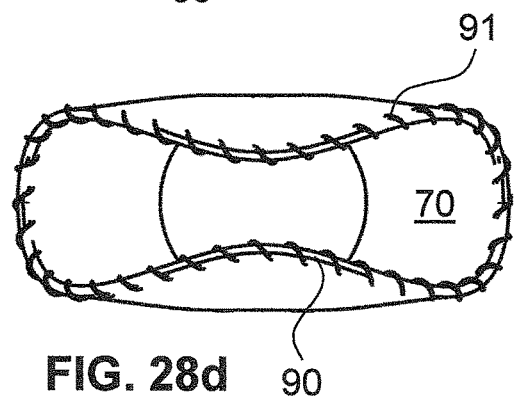

FIGS. 28a to 28d show an additional embodiment of a graft 7. It is similar to the one of FIGS. 27a to 27d, i.e. it has also a widened reinforced end. However, the shape of the end is slightly different. In the cross-side view as shown in FIG. 28c, the end has a round, but not closed shape. In the top view as shown in FIG. 28b, it has an almost semi-circular shape. In a preferred embodiment, it comprises two mirror-symmetrical parts. In the preferred embodiment shown in FIG. 28d, it looks like a mouth.

FIGS. 29 to 32 show another embodiment of the intervention kit according to the present invention. The intervention is similar to the one described above; therefore some steps are not shown again. This kit does also comprise a first catheter 10' and a first hollow needle 20 for introduction into the RIVA R and a second catheter 11 and a second hollow needle 21 for introduction into the LIMA L. however, the first catheter 10' is a balloon catheter with an inflatable delivery end forming a balloon 40'.

Figure 29:
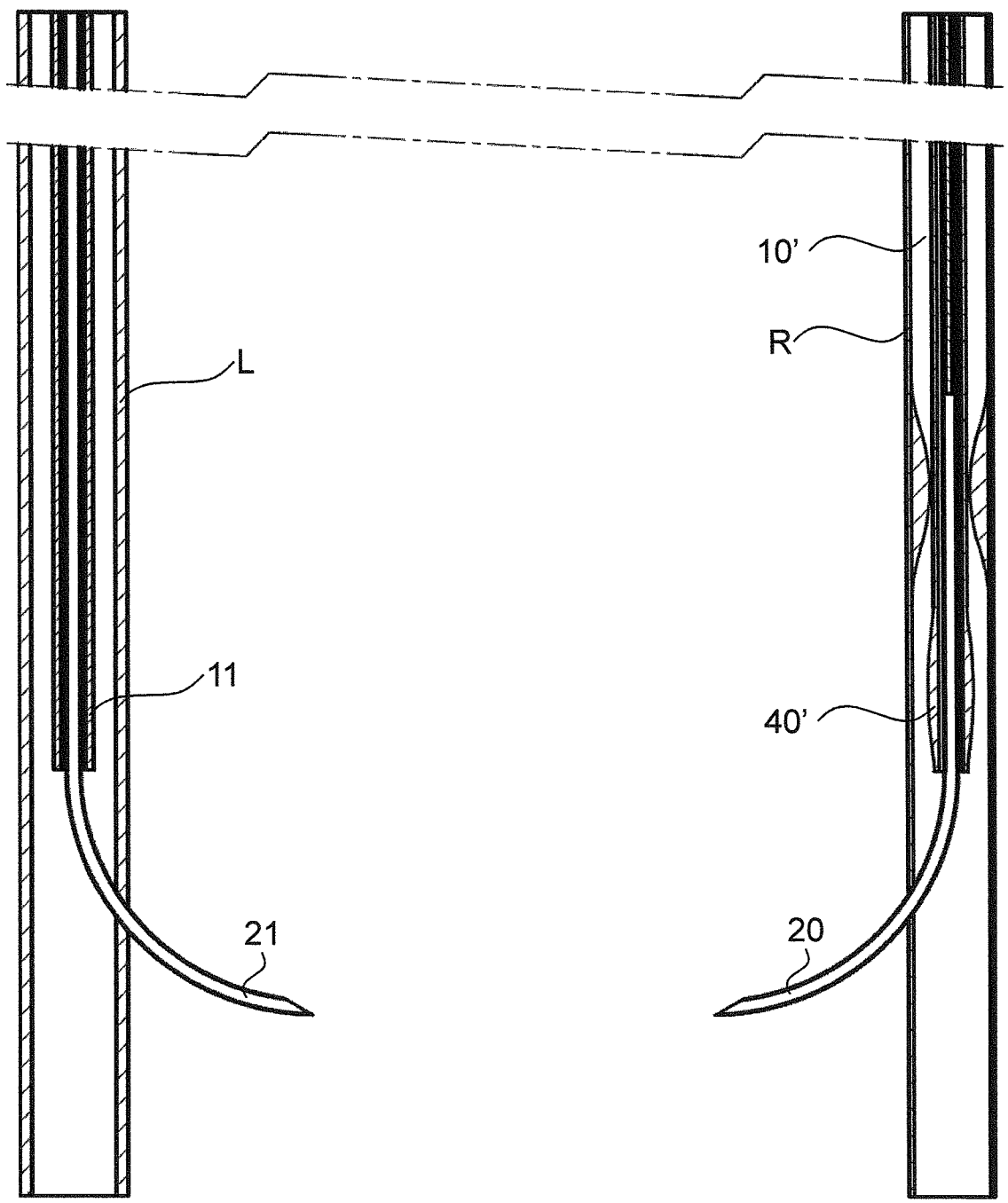
FIGS. 29 to 32 the intervention kit according to a second embodiment of the invention in use, when placing a bypass between LIMA and RIVA.

As shown in FIG. 29, a first catheter 10' is introduced into the RIVA R, passing the occlusion. The first needle 20 is passed within the first catheter 10', punctures the RIVA R and is moved through this puncture towards the LIMA L. A first guide wire 30 is moved within the first needle 20. On the LIMA L side the second catheter 11 is entered, the second needle 21 is moved within the second catheter and punctures the LIMA L. The second needle 21 is moved through the puncture towards the RIVA R.

Figure 30:
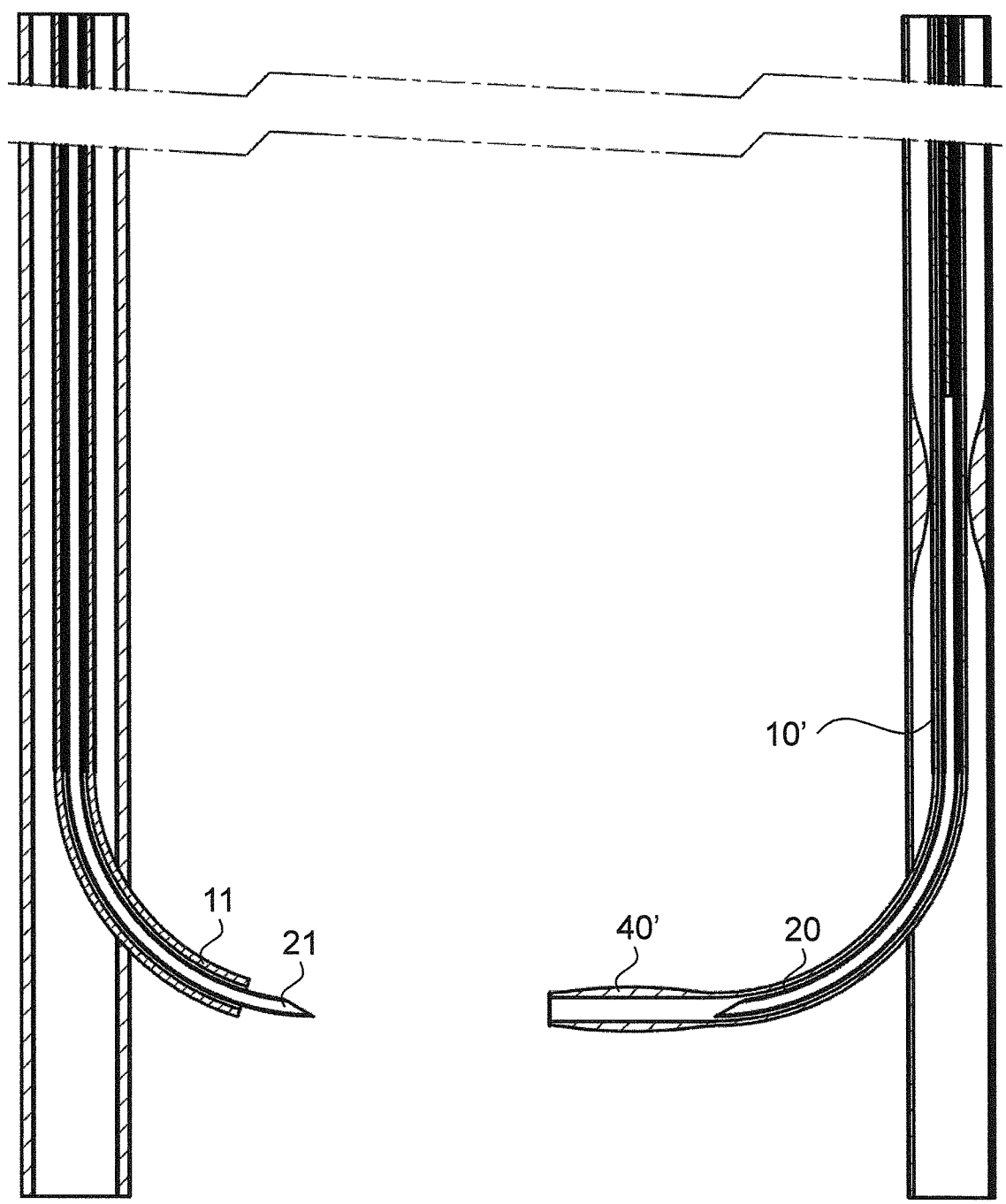

In the next step, the two catheters 10', 11 are moved over the respective needles 20, 21 through the respective punctures towards each other, as can be seen in FIG. 30. This step is different to the first embodiment.

Figure 31:
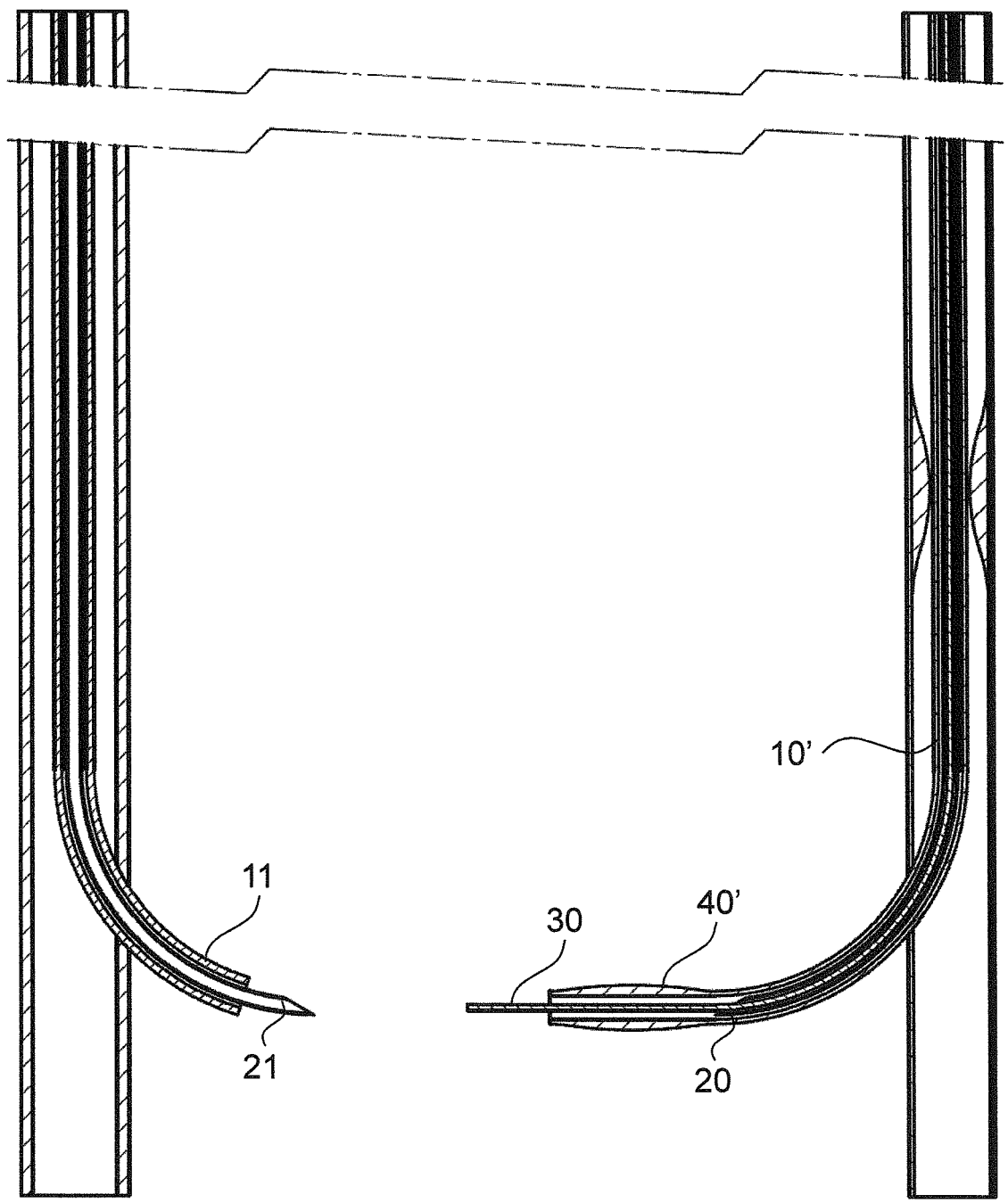
Figure 32:
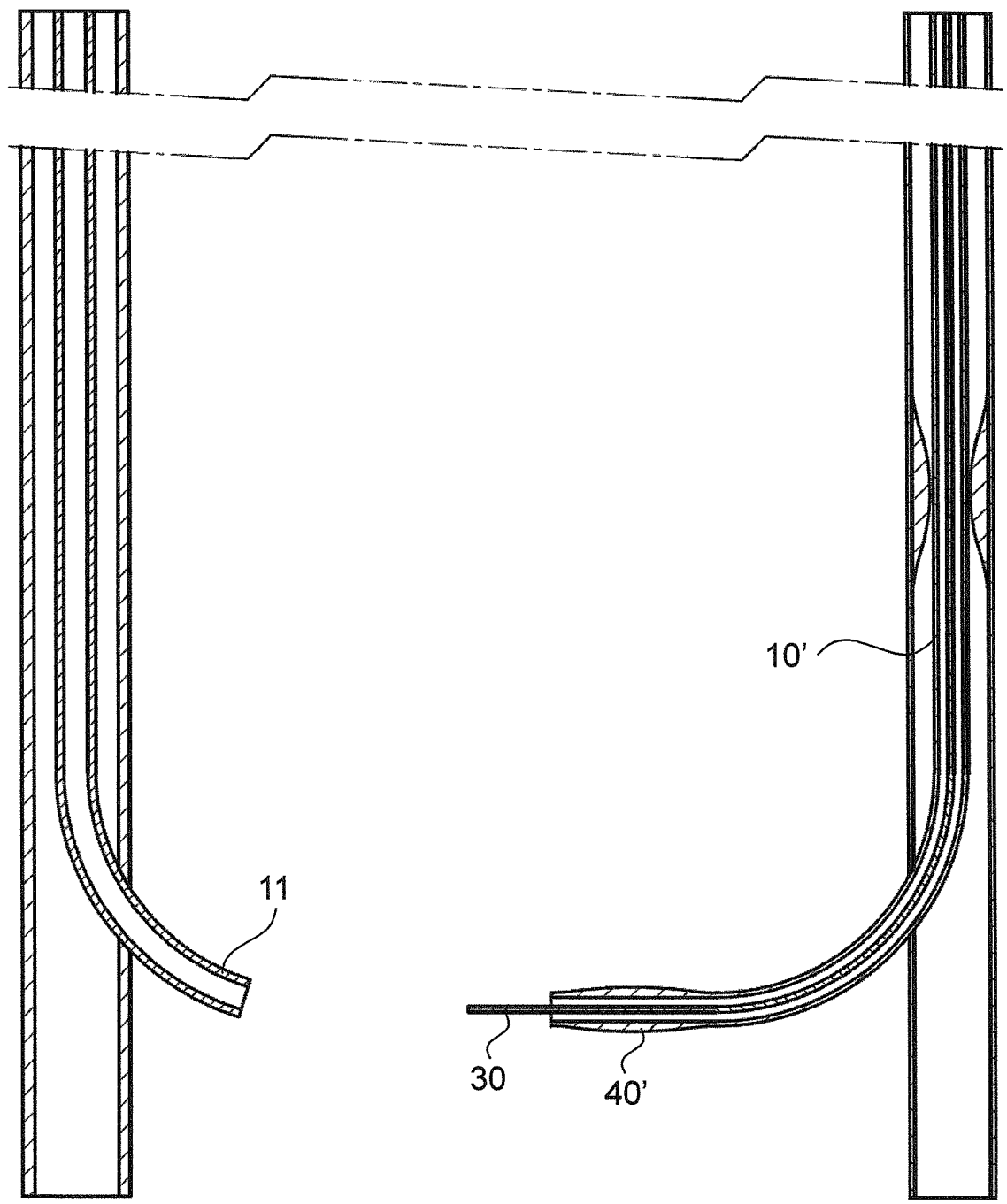
Figure 33:
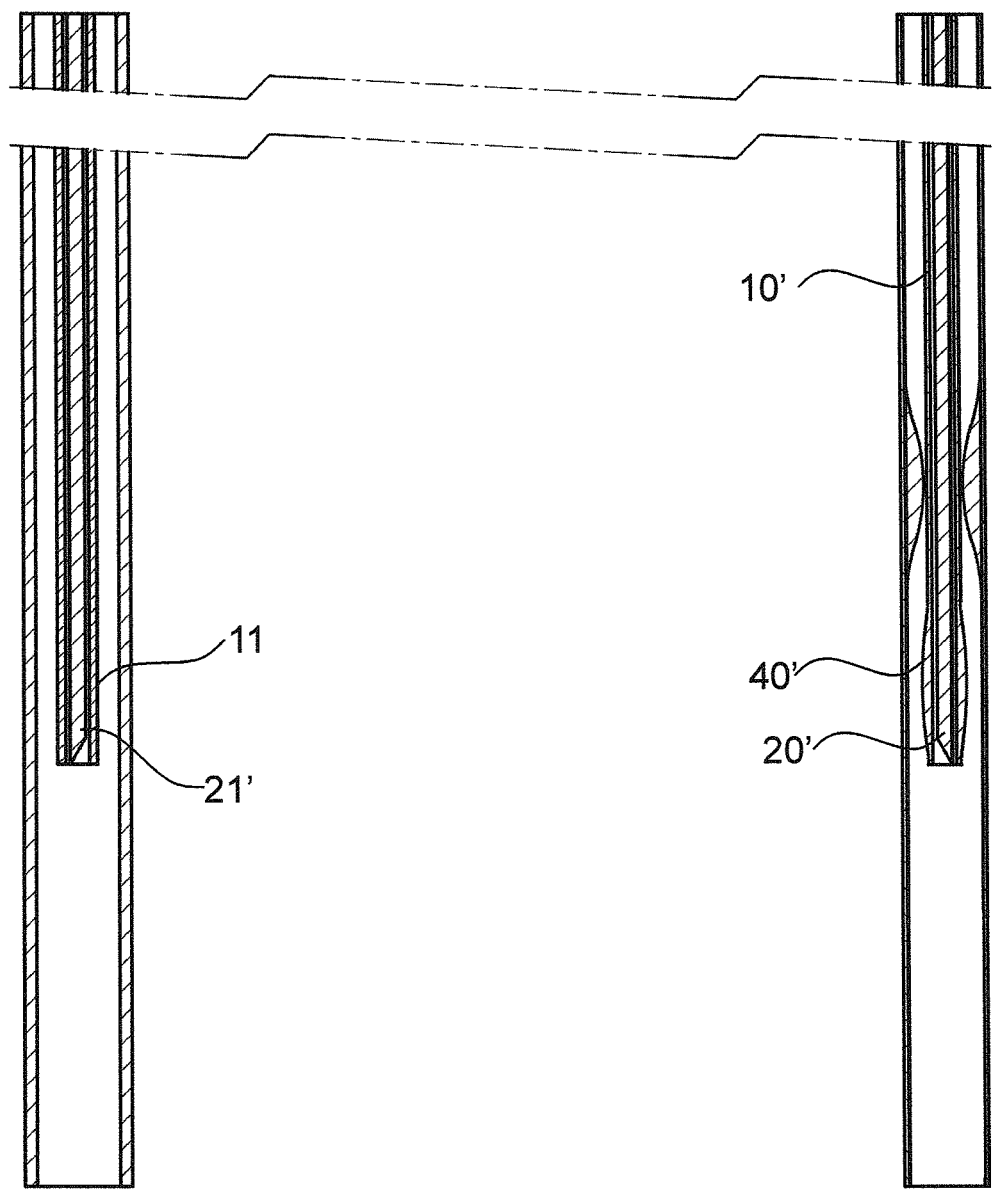
FIGS. 33 to 37 the intervention kit according to a third embodiment of the invention in use, when placing a bypass between LIMA and RIVA

In the step according to FIG. 31 the first guide wire 30 is forwarded within the first needle so that his first end protrudes the first catheter 10'. The first needle 20 is then retracted and moved out of the RIVA R and the patient's body. The second needle 21 is retracted and moved out of the LIMA L and the patient's body as well. This situation is shown in FIG. 31.

Figure 6:
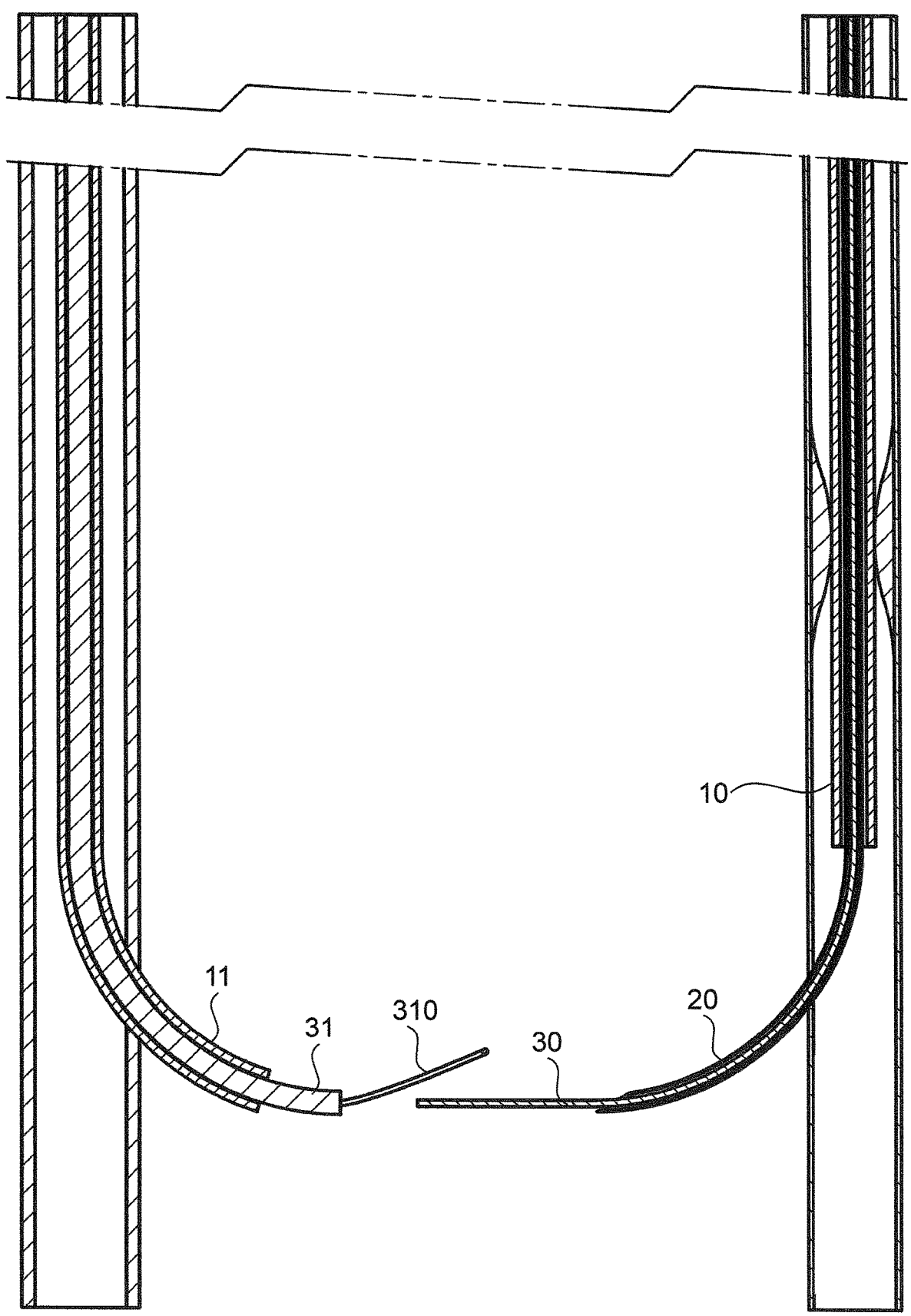
Figure 7:
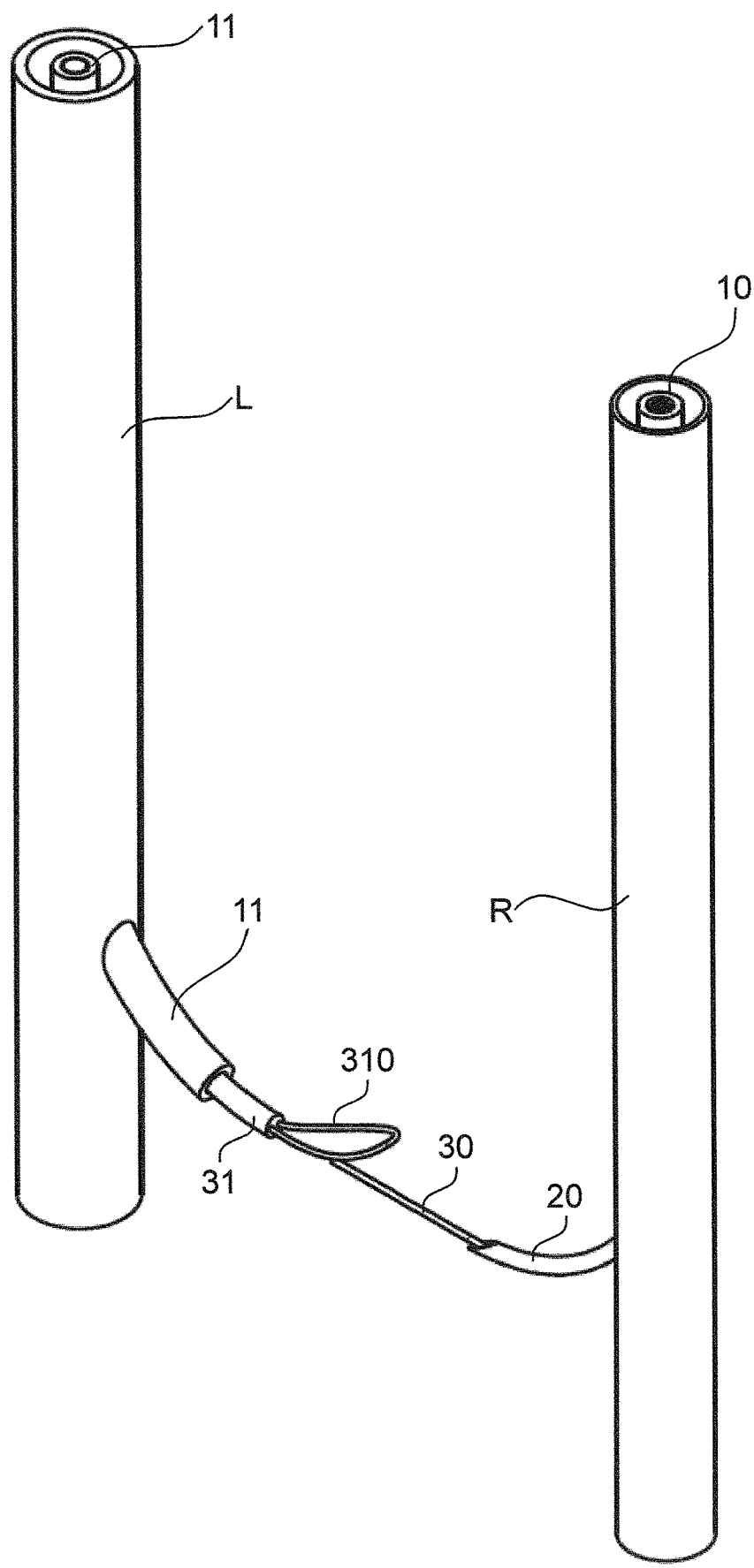
Figure 8:
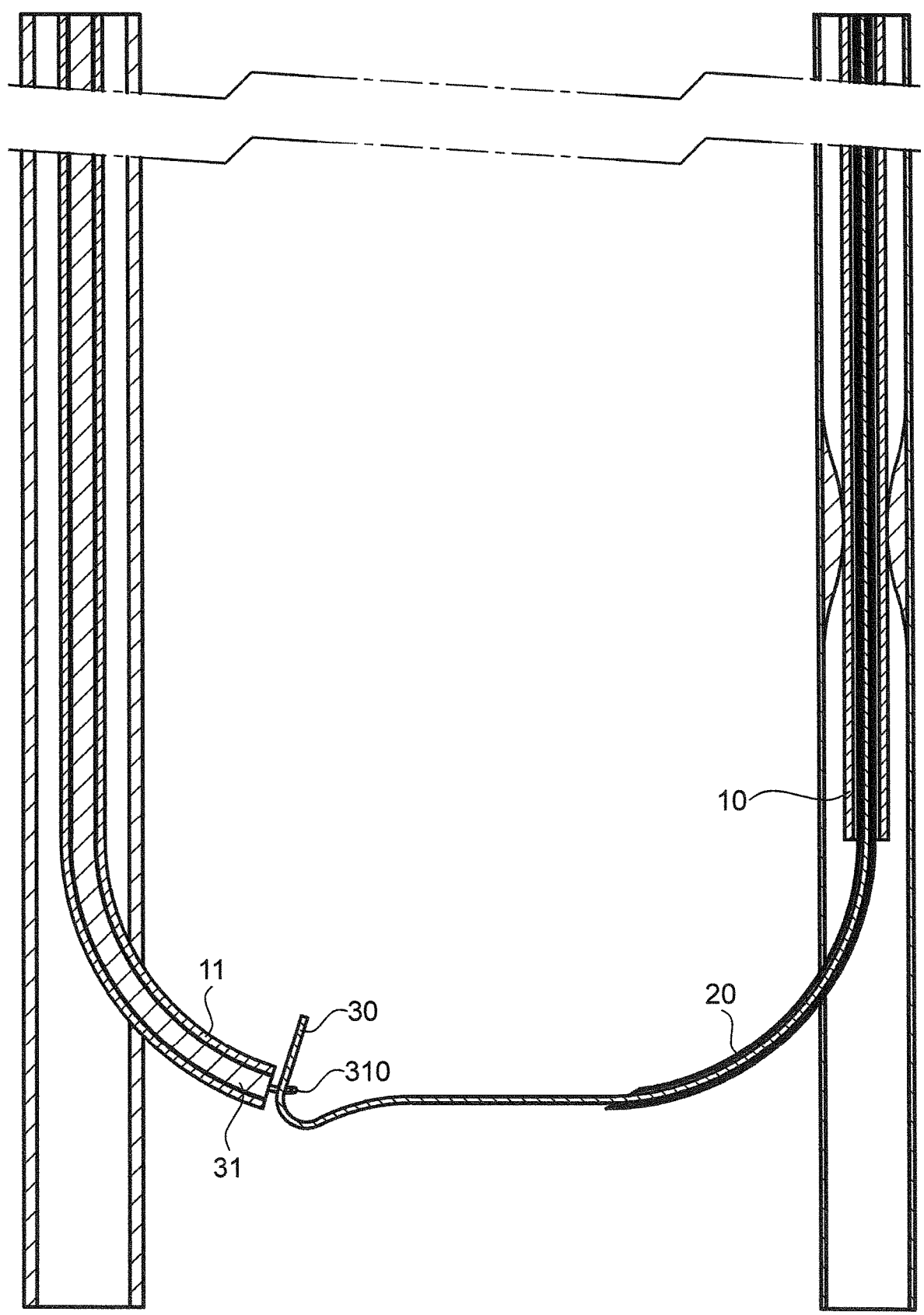
Figure 9:
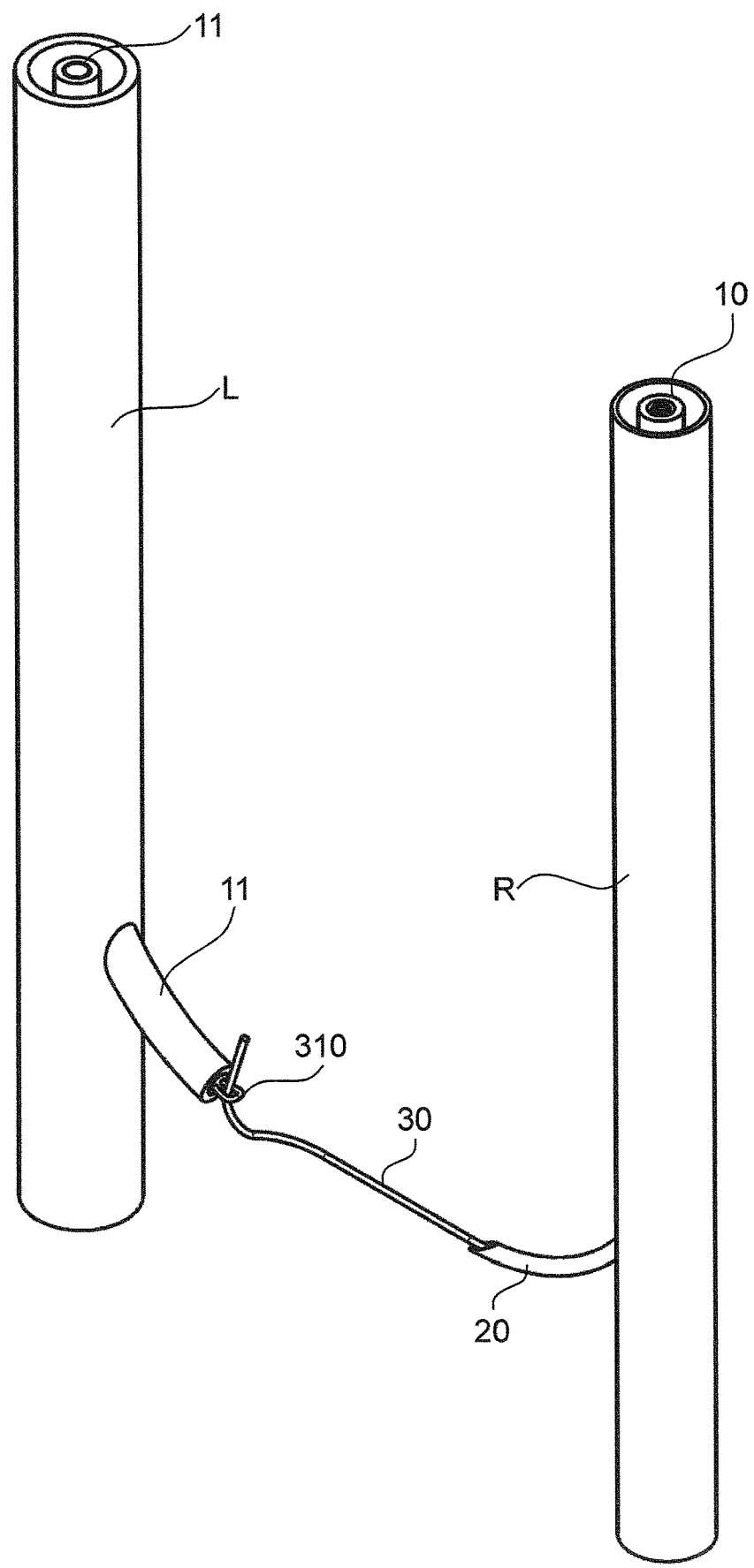

In the next step, the second guide wire 31 as shown in FIG. 6 is moved within the second catheter 11 towards the first guide wire 30. The two guide wires 30, 31 are formed as previously described, one of them for example formed as a lasso as shown in FIG. 7. The first guide wire 30 is caught by the second guide wire 31 as shown in FIGS. 8 and 9. The first guide wire 30 is moved through the second catheter 11 into the LIMA L until this end reaches the outside of the patient's body. The first catheter 10' still remains in the place as shown in FIG. 31. The second catheter 11 is removed out of the LIMA L and out of the patient's body, with the first catheter 10' still remaining in the place shown in FIG. 32. There, this situation now corresponds to the one shown in FIG. 13, the first catheter 10' being the balloon catheter 4, 40 of the first embodiment. The following steps are identical to the ones of FIGS. 14 to 23 and are not shown or described again.

The advantage of this second embodiment is that no exchange between a first catheter and a balloon catheter is needed. The first catheter is already the balloon catheter. The amount of items and the amount of intervention steps are reduced, both saving costs and time and minimizing the risk.

Figure 34:
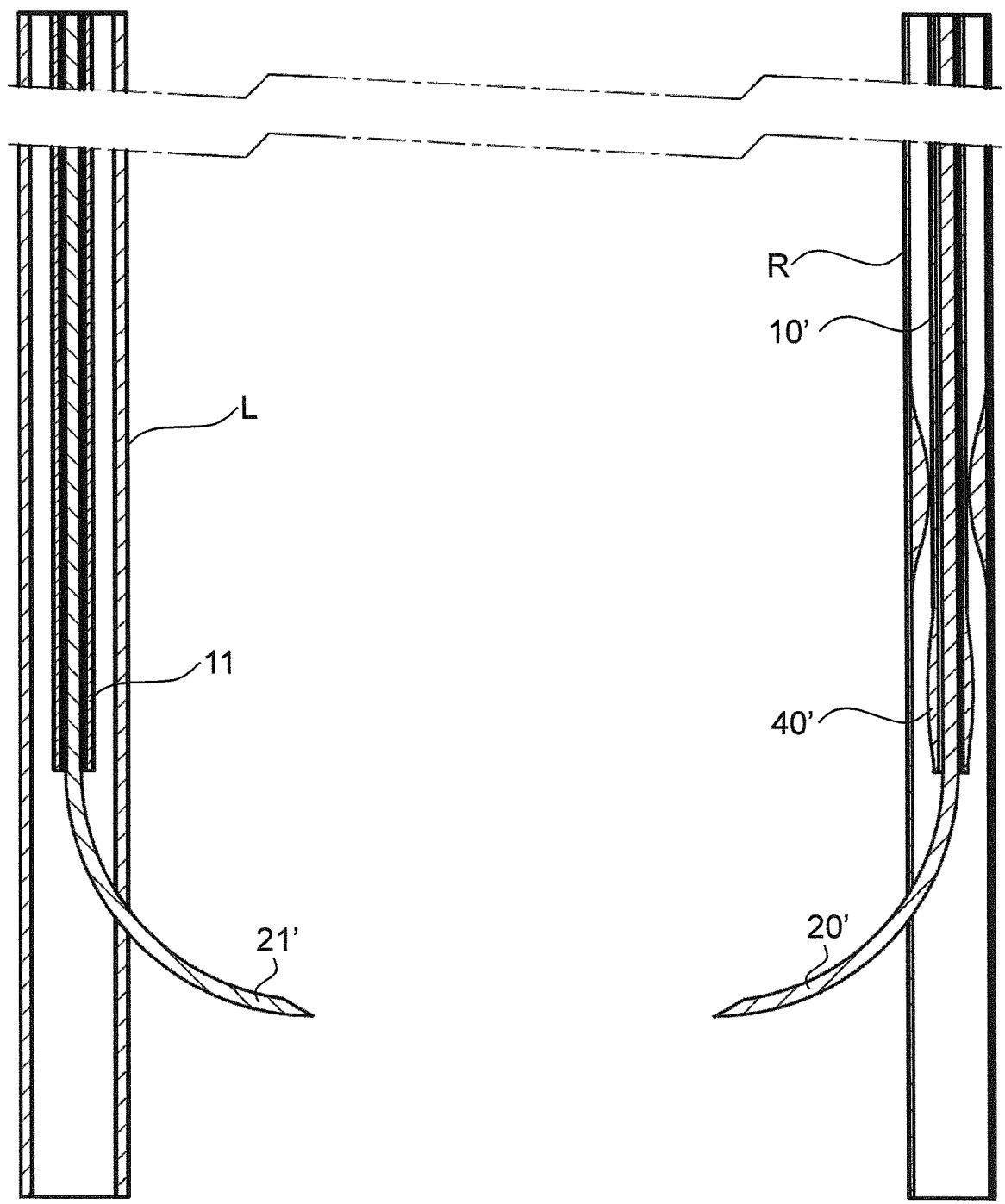
Figure 35:
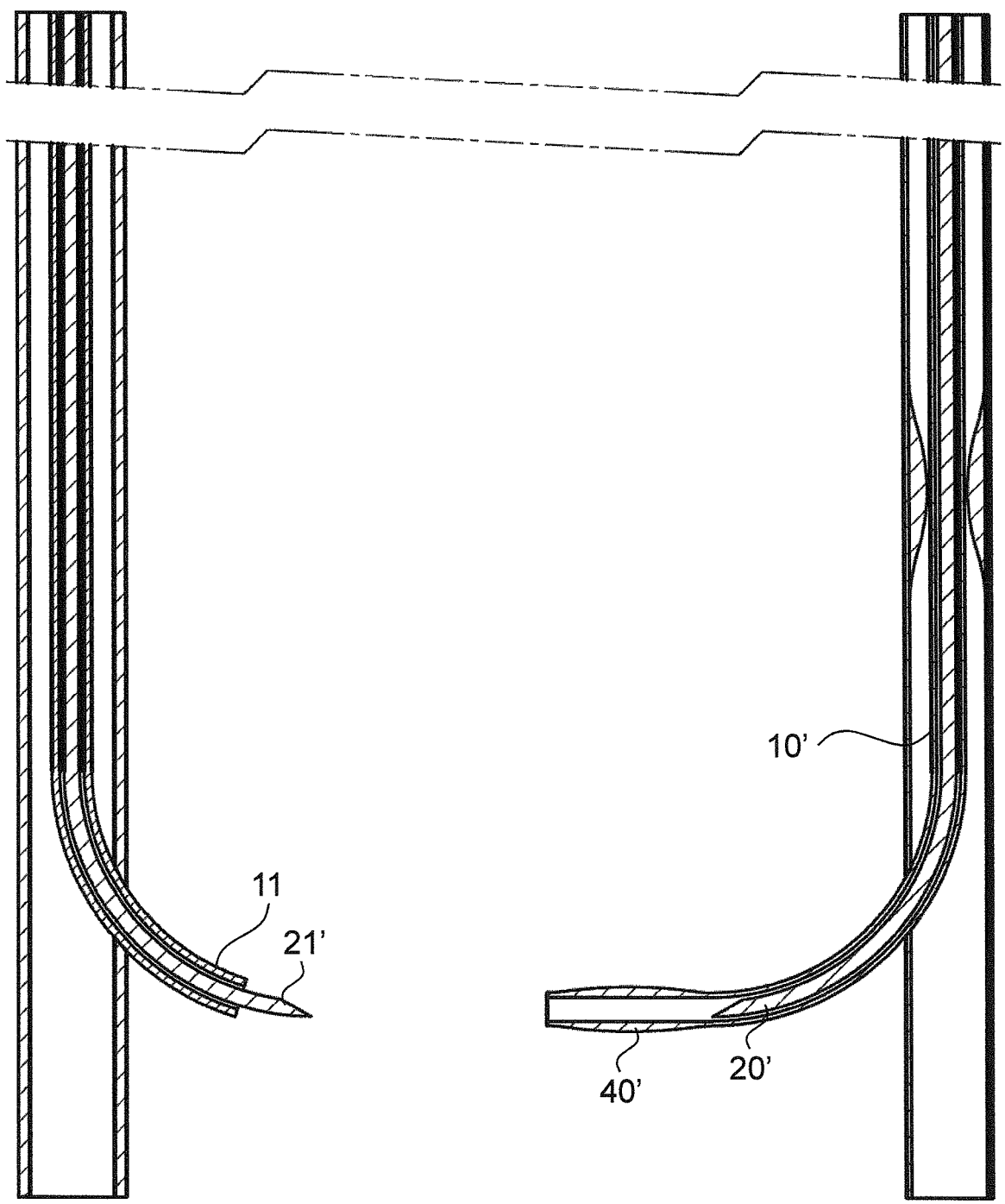
Figure 36:
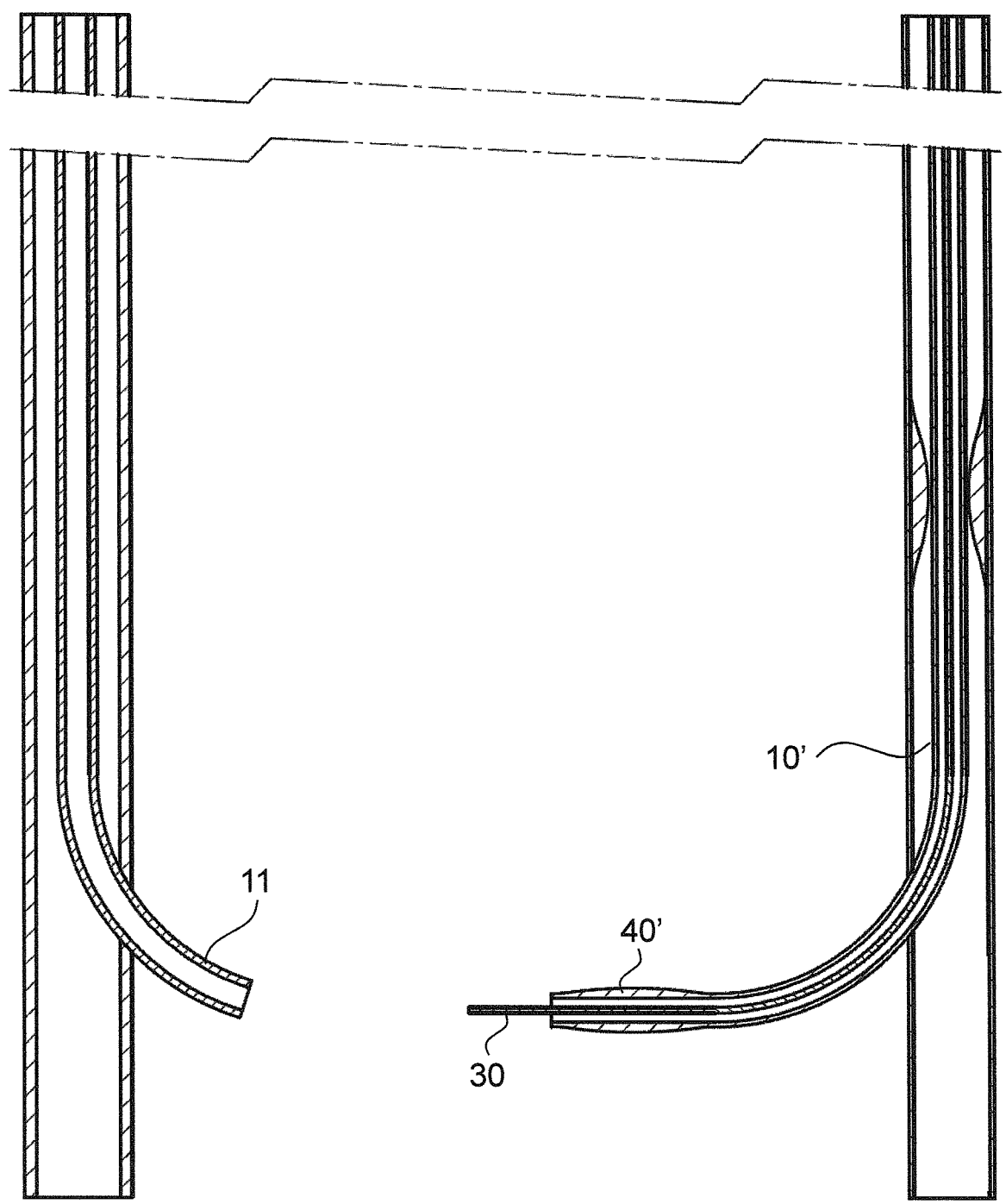
Figure 37:
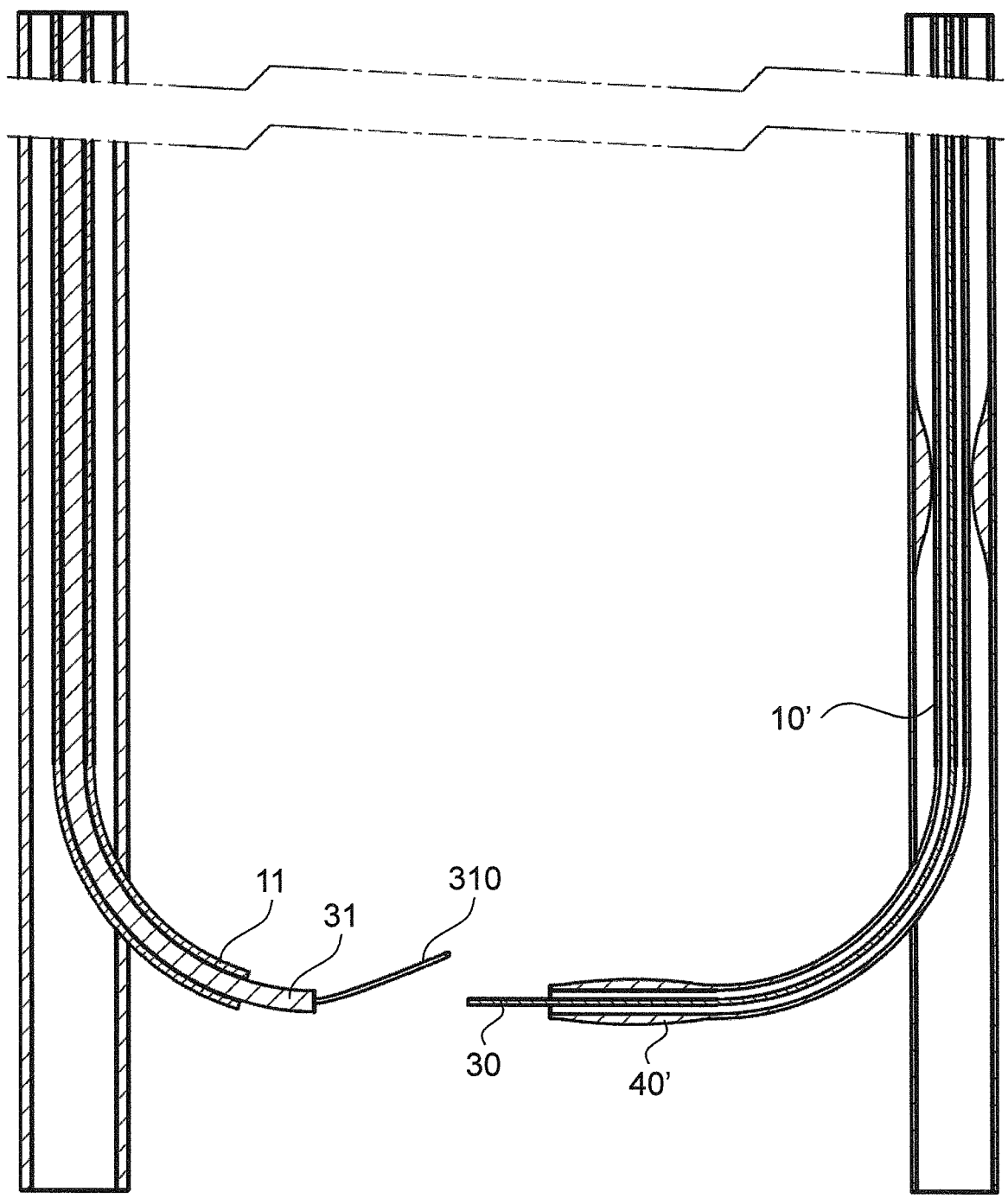

FIGS. 33 to 37 show even another embodiment of the inventive kit. The needles 20', 21' are not hollow but solid. They are once again introduced by using a first and a second catheter 10', 11 respectively. The first catheter 10' is once again a balloon catheter. The puncturing of the LIMA L and the RIVA R takes place like in the first and second embodiment. It is shown in FIG. 34. The needles 20', 21' and the catheters 10', 11 are forwarded and pushed through the punctures as in the second embodiment. This is shown in FIG. 35. The solid needles 20', 21' are then removed and the first guide wire 30 is forwarded through the first catheter 10' as shown in FIG. 36. This step differs from the according step of the second embodiment shown in FIG. 30. The second guide wire 31 is forwarded through the second catheter 11 to catch the first guide wire 30 as shown in FIG. 37. The following steps are identical with the ones of the first and second embodiment and are not described or shown.

All three embodiments can use straight or curved needles. In addition, one of the two needles can be curved, the other can be straight. Furthermore, the solid needles can also be used with the normal catheter and separate balloon catheter as described in the first embodiment. In addition, in all embodiments, one needle can be solid and the other can be hollow.

Figure 38:
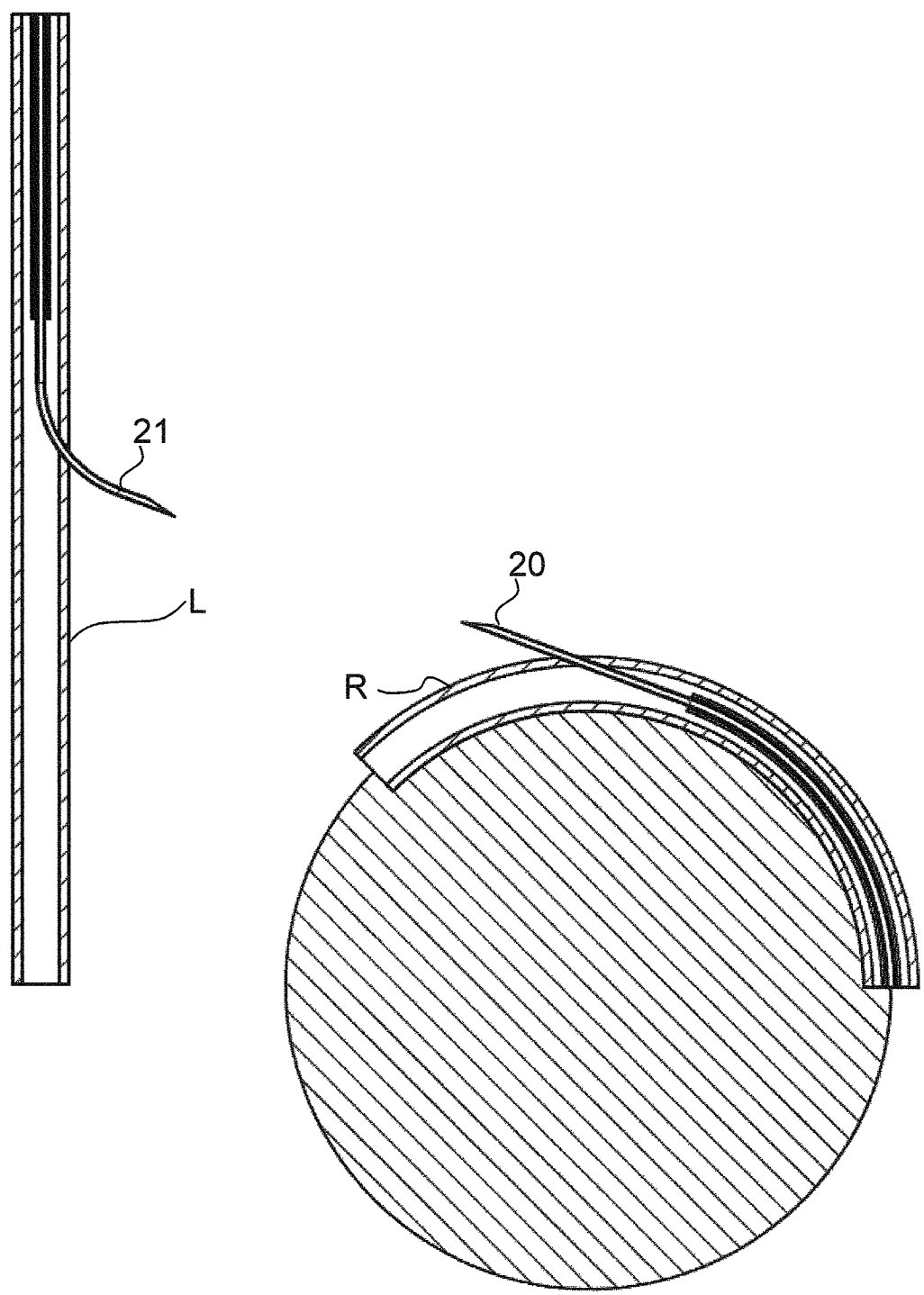
FIG. 38 shows an embodiment of an inventive kit with a straight and a curved needle.

FIG. 38 shows an embodiment where the first needle 20 is straight and the second needle 21 is curved.

The invention also comprises a kit with two catheters, two guide wires and two needles but not expansible element such as a balloon catheter. Each needle is puncturing a vessel from the inside. The first guide wire is captured by the second guide wire as described above and moved along the second catheter. However, the bypass element delivery system is moved along the first guide wire to form a bridge between the two punctures by other means known in the state of the art.

The inventive intervention kit enables an atraumatic placing of a bypass. The clogged vessel has to be closed only for a minimum of time, wherein the punctures remain closed.

LIST OF REFERENCE SIGNS

| | | | |
|---|---|---|---|
| 10, 10' | first catheter | 6 | stent |
| 100 | first delivery end | 60 | end |
| 11 | second catheter | 61 | spike |
| 110 | second delivery end | 62 | hook |
| 20, 20' | first needle | 7 | graft |
| 200 | first cutting edge | 70 | widened end |
| 21, 21' | second needle | 8 | inner catheter of the delivery system |
| 210 | second cutting edge | | |
| 30 | first guide wire | 80 | plunger |
| 300 | first end region | 90 | reinforcing ring |
| 31 | second guide wire | 91 | thread |
| 310 | catch | L | LIMA (left internal mammary artery) |
| 4 | balloon tail | | |
| 40, 40' | balloon | R | RIVA (ramus interventricularis anterior) |
| 50 | stop collar | | |
| 51 | connecting end | O | blockage |

| | LIST OF REFERENCE SIGNS |
|---|---|
| 52 | delivery system casing |
| 53 | delivery system catheter |

The invention claimed is:

1. A kit for placing a bypass between a first body vessel and a second body vessel of a patient, the kit comprising:
   a first catheter to be placed within the first body vessel, the first catheter having a first delivery end, and a second catheter to be placed within the second body vessel, the second catheter having a second delivery end,
   a first guide wire moveable within the first catheter, the first guide wire having a first end region being moveable to the first delivery end, the first guide wire having an opposite end being opposite to the first end region,
   a second guide wire moveable within the second catheter, the second guide wire having a second end being moveable to the second delivery end, the second end of the second guide wire being a catch for capturing the first guide wire and for moving the first guide wire into the second catheter and within the second body vessel with a first end region of the first guide wire first, and
   a bypass element delivery system for holding a bypass element and an expansible element, the expansible element being separate from the bypass element delivery system and the bypass element delivery system being moveable without the expansible element along the first guide wire within the second body vessel starting from the first end region of the first guide wire, wherein the bypass element delivery system is capable of releasing and setting free the bypass element,
   the expansible element being capable of moving in a direction from the first body vessel to the first end region of the first guide wire without the bypass element delivery system, thereby being capable of connecting with the bypass element delivery system and of moving the bypass element delivery system towards the opposite end of the first guide wire and towards the first body vessel, and
   wherein the expansible element is capable of releasing the bypass element delivery system for setting the bypass element delivery system free.

2. The kit of claim 1 wherein the expansible element is capable of pulling the bypass element delivery system towards the opposite end of the first guide wire.

3. The kit of claim 1 wherein the expansible element is capable of releasing the bypass element delivery system for setting the bypass element delivery system free, while the bypass element delivery system is holding the bypass element and is capable of afterwards releasing and setting free the bypass element.

4. The kit of claim 1 wherein the expansible element is movable along the first guide wire from the opposite end of the first guide wire towards the first end region of the first guide wire.

5. The kit of claim 1 wherein the expansible element is formed by the first catheter.

6. The kit of claim 1 wherein the expansible element is a balloon, wherein the bypass element delivery system comprises a connecting end, wherein the balloon is inflatable within the connecting end of the bypass element delivery system for capturing the bypass element delivery system and wherein the balloon is deflatable for releasing the connecting end of the bypass element delivery system and for setting the bypass element delivery system free.

7. The kit of claim 1 wherein the expansible element is slippable over the first guide wire and is moveable relative to the first guide wire.

8. The kit of claim 1 wherein the catch is one of a loop, a forceps and a hook.

9. The kit of claim 1 wherein the bypass element delivery system is moveable along the first guide wire in the absence of the second guide wire.

10. The kit of claim 1 wherein the kit further comprises a bypass element for connecting the second body vessel with the first body vessel, the bypass element comprising one or both of a stabilization structure and a graft.

11. The kit of claim 10 wherein the bypass element comprises the stabilization structure and the graft and wherein the stabilization structure encompasses the graft.

12. The kit of claim 1 wherein the kit further comprises a first needle moveable within the first catheter to the first delivery end and a second needle moveable within the second catheter to the second delivery end.

13. The kit of claim 12 wherein the first guide wire is moveable within and relative to the first needle.

14. A bypass element to be held in a bypass element delivery system, the bypass element delivery system being part of a kit for placing the bypass element between a first body vessel and a second body vessel of a patient, wherein the kit comprises:
   a first catheter with a first delivery end and a second catheter with a second delivery end,
   a first guide wire moveable within the first catheter, the first guide wire having a first end region being moveable to the first delivery end, the first guide wire having an opposite end being opposite to the first end region,
   a second guide wire moveable within the second catheter, the second guide wire having a second end being moveable to the second delivery end, the second end of the second guide wire being a catch for capturing the first guide wire and for moving the first guide wire into the second catheter with a first end region of the first guide wire first, and
   the bypass element delivery system for holding the bypass element, the bypass element delivery system being moveable along the first guide wire starting from the first end region of the first guide wire, wherein the bypass element delivery system is capable of releasing and setting free the bypass element,
   wherein the kit comprises an expansible element, the expansible element being capable of connecting with the bypass element delivery system and of moving the bypass element delivery system towards the opposite end of the first guide wire, and
   wherein the expansible element is capable of releasing the bypass element delivery system for setting the bypass element delivery system free,
   wherein the bypass element comprises a stabilization structure and a graft arranged concentrically to each other, wherein the stabilization structure encompasses the graft,
   wherein the graft comprises at least one end forming a widening, the widening being reinforced with a ring and acting as an anchoring element and wherein the shape of the widened end and the ring is generally oval and wherein the shape of the widened end and the ring are configured to snuggle and thereby cling to an inner surface of the first body vessel surrounding a puncture of the first body vessel when the widened end and the ring are located within the first body vessel.

15. A method for placing a bypass between a first body vessel and a second body vessel of a patient, the method comprising the following steps:
providing a first catheter within the first body vessel, the first catheter having a first delivery end,
providing a second catheter within the second body vessel, the second catheter having a second delivery end,
providing a first needle and a second needle,
providing a first guide wire having a first end region and an opposite end being opposite to the first end region,
moving said first catheter within the first body vessel and moving said first needle within said first catheter and puncturing said first vessel from an inside of the first vessel,
moving said second catheter within the second body vessel and moving said second needle within said second catheter and puncturing said second vessel from an inside of the second vessel,
moving said first guide wire within the first catheter, thereby moving the first end region to the first delivery end,
providing a second guide wire having a second end, the second end being a catch,
moving said second guide wire within the second catheter, thereby moving the catch to the second delivery end,
capturing the first end region with the catch and moving the captured first guide wire into the second catheter and within the second body vessel with the first end region first,
providing a bypass element delivery system and a bypass element, the bypass element delivery system holding the bypass element,
providing an expansible element, the expansible element being separate from the bypass element delivery system,
moving the bypass element delivery system without the expansible element within the second body vessel and along the first guide wire starting from the first end region of the first guide wire,
moving the expansible element without the bypass element delivery system along the first guide wire in a direction from the first body vessel to the first end region of the first guide wire,
connecting the bypass element delivery system with the expansible element and moving the bypass element delivery system towards the opposite end of the first guide wire and towards the first body vessel,
releasing the bypass element delivery system from the expansible element, and
releasing the bypass element from the bypass element delivery system and setting free the bypass element.

* * * * *